(12) United States Patent
Arguello et al.

(10) Patent No.: US 6,500,614 B1
(45) Date of Patent: Dec. 31, 2002

(54) METHOD FOR IDENTIFYING AN UNKNOWN ALLELE

(75) Inventors: Rafael Arguello, London (GB); Hovanes Avakian, London (GB); Alejandro Madrigal, London (GB)

(73) Assignee: The Anthony Nolan Bone Marrow Trust, London (GB)

( * ) Notice: Subject to any disclaimer, the term of this patent is extended or adjusted under 35 U.S.C. 154(b) by 0 days.

(21) Appl. No.: 09/077,619

(22) PCT Filed: Nov. 29, 1996

(86) PCT No.: PCT/GB96/02959
§ 371 (c)(1),
(2), (4) Date: Mar. 21, 2000

(87) PCT Pub. No.: WO97/20197
PCT Pub. Date: Jun. 5, 1997

(30) Foreign Application Priority Data

Nov. 29, 1995 (GB) .............................................. 9524381

(51) Int. Cl.$^7$ .......................... C12Q 1/68; C12P 19/34; C07H 21/02; C07H 21/04
(52) U.S. Cl. ......................... 435/6; 435/91.1; 536/23.1; 536/23.5; 536/24.3; 536/24.33
(58) Field of Search ......................... 435/6, 91.1, 23.1, 435/23.5, 24.3, 24.33; 536/23.1, 24.3, 24.33

(56) References Cited

U.S. PATENT DOCUMENTS 5,451,512 A * 9/1995 Apple et al. ................ 435/91.2

FOREIGN PATENT DOCUMENTS

| EP | 0 543 222 A1 | 11/1992 |
|---|---|---|
| EP | 0 543 222 A1 | 5/1993 |
| WO | WO 89/11547 | 1/1989 |
| WO | WO 89/11547 | 11/1989 |
| WO | WO 92/07956 | * 5/1992 |
| WO | WO 92/10589 | 6/1992 |
| WO | WO 93/05179 | 3/1993 |

OTHER PUBLICATIONS

Dyer P. A. et al., "HLA Allele Detection Using Molecular Techniques", Disease Markers, vol. 11, pp. 145–160 (1993).*

Eiermann, T. H., et al., "HLA–DPB1 oligonucleotide typing of a Southwest German Caucasian population," Tissue Antigens, 38, pp. 193–198 (1991); Munksgaard International Publishers, Ltd.

Landegren, U., "Detection of Mutations in Human DNA," Genetics Analysis Techniques and Applications, vol. 9, No. 1, Feb. 1, 1992, pp. 3–8; Elsevier Science Publishing Co., Inc.

Zimmerman, P., "Exploiting structural differences among heteroduplex molecules to simplify genotyping the DQA1 and DQB1 alleles in human lymphocyte typing," Nucleic Acids Research, vol. 21, No. 19, pp. 4551–4547 (1993); Oxford University Press.

Grompe, M., "The rapid detection of unknown mutations in nucleic acids," Nature Genetics, vol. 5, pp. 112–117 (Oct. 1993); Macmillian Magazines, Ltd.

Gao, X., et al., "Characterization of the HLA–A Polymorphism by Locus–Specific Polymerase Chain Reaction Amplification and Oligonucleotide Hybridization," Human Immunology, vol. 41, pp. 267–279 (1994); Elsevier Science Publishing Co., Inc.

Allen, M. et al., "A Comprehensive Polymerase Chain Reaction–Oligonucleotide Typing System for the HLA Class I A Locus," Human Immunology, vol. 40, pp. 25–32 (1994); Elsevier Science Publishing Co., Inc.

Zimmerman, P., et al., "Migration of a Novel DQA1* Allele (DQA1*0502) from African Origin to North and South America," Human Immunology, vol. 42, pp. 233–240 (1995); Elsevier Science Publishing Co., Inc.

Zimmerman, P. et al., "Optimizing Probe Selection in Directed Heteroduplex Analysis Using HDProbe 1.1," BioTechniques, vol. 19, pp. 972–977 (Dec. 1995); Eaton Publishing Co.

Arguello, R., et al., "A novel method for simultaneous high reslution identification of HLA–A, HLA–B, and HLA–Cw alleles," Proc. Natl. Acad. Sci. USA, vol. 93, pp. 10961–10965 (Oct. 1996); National Academy of Sciences.

Allen et al., "A Comprehensive Polymerase Chain Reaction—Oligonucleotide Typing System for the HLA Class I A Locus", Human Immunology 40:25–32 (1994).

Arguello et al., "A Novel Method for Simultaneous High Resolution Identification of HLA–A, HLA–B, and HLA–Cw Alleles", Proc. Natl. Acad. Sci. 93:10961–10965.

Eiermann et al., "HLA–DPB1 Oligonucleotide Typing of a Southwest German Caucasian Population", Tissue Antigens 38:193–198 (1991).

(List continued on next page.)

Primary Examiner—Kenneth R. Horlick
Assistant Examiner—Teresa Strzelecka
(74) Attorney, Agent, or Firm—Medlen & Carroll, LLP

(57) ABSTRACT

The invention provides a method for identifying an unknown allele of a polyallelic gene, which method comprises (i) contacting the unknown allele with a panel of probes, each of which recognises a sequence motif that is present in some alleles of the polyallelic gene but not in others; (ii) observing which probes recognise the unknown allele so as to obtain a fingerprint of the unknown allele; and (iii) comparing the fingerprint with fingerprints of known alleles. The use of a panel of probes which each recognises a different motif allows identification of which motifs are present in the unknown allele. The alleles of the polyallelic gene each have a unique combination of motifs and so identification of this combination (or "fingerprint") leads to identification of the unknown allele.

14 Claims, 4 Drawing Sheets

OTHER PUBLICATIONS

Gao et al., "Characterization of the HLA–A Polymorphism by Locus–Specific Polymerase Chain Reaction Amplification and Oligonucleotide Hybridization", *Human Immunology* 41:267–279 (1994).

Grompe, Markus, "The Rapid Detection of Unknown Mutations in Nucleic Acids", *Nature Genetics* 5:112–117 (1993).

Landegren, Ulf, "Detection of Muatations in Human DNA", *Gen. Analysis Tech. And Appl.*, 9(1):3–8 (1992).

Zimmerman et al., "Exploiting Structural Differences Among Heteroduplex Molecules to Simplify Genotyping the DQA1 and DQB1 Alleles in Human Lymphocyte Typing", *Nucleic Acids Research* 21(19):4541–4547 (1993).

Zimmerman et al., "Migration of a Novel DQA* Allele (DQA1*0502) from African Origin to North and South America", *Human Immunology* 42:233–244 (1995).

Zimmerman et al., "Optimizing Probe Selection in Directed Heteroduplex Analysis Using HDProbe 1.1", *BioTechniques* 19:972–977 (1995).

* cited by examiner

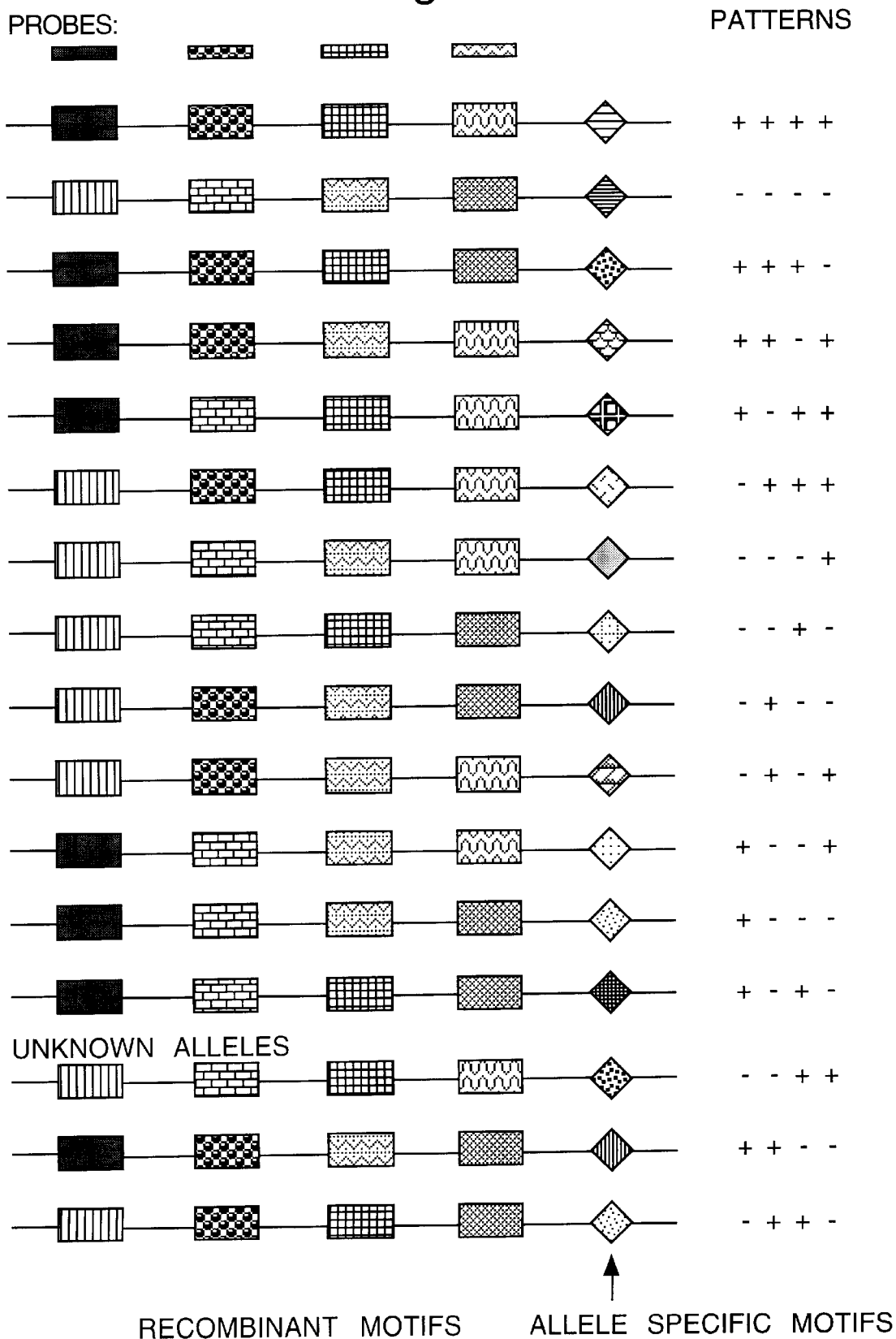

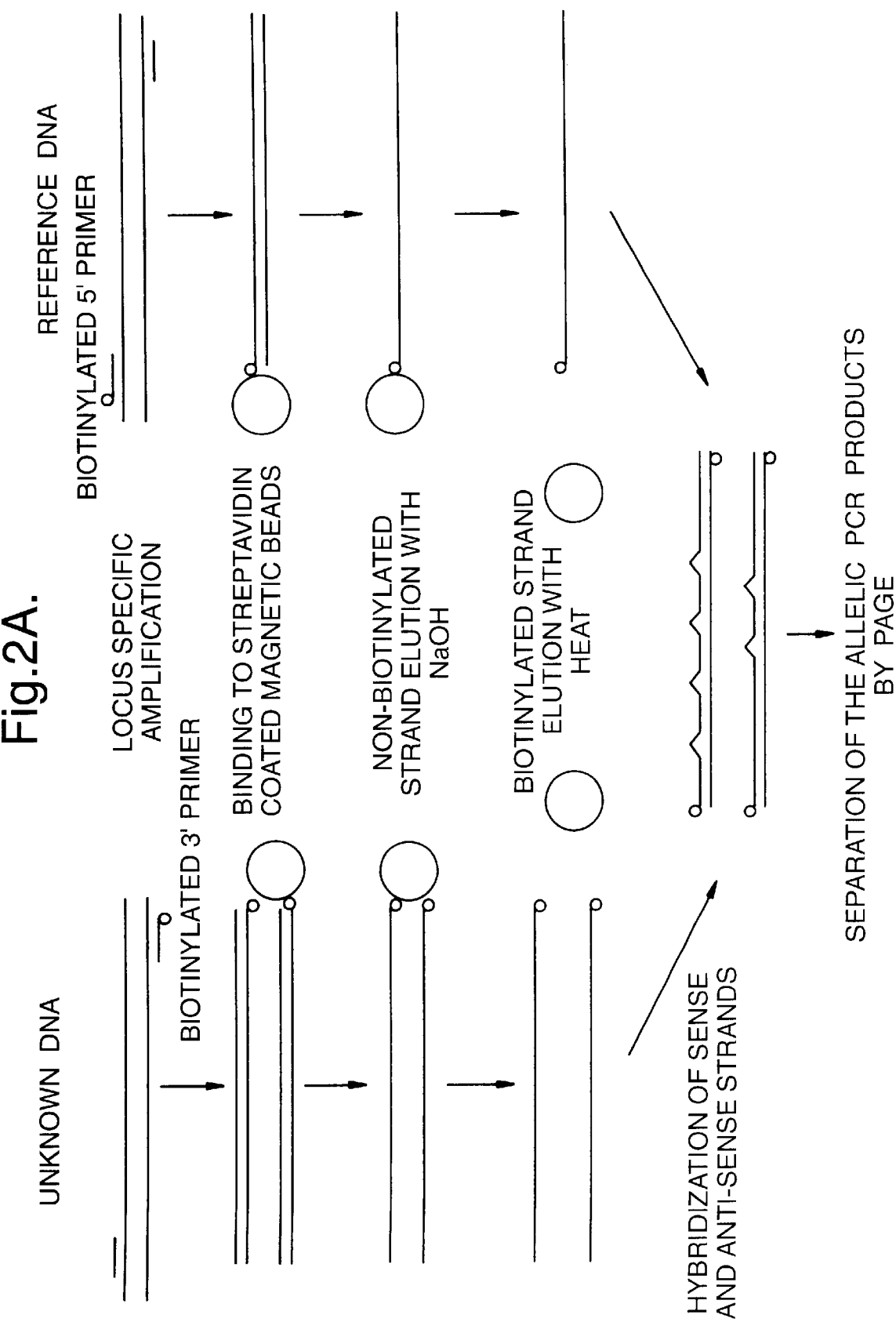

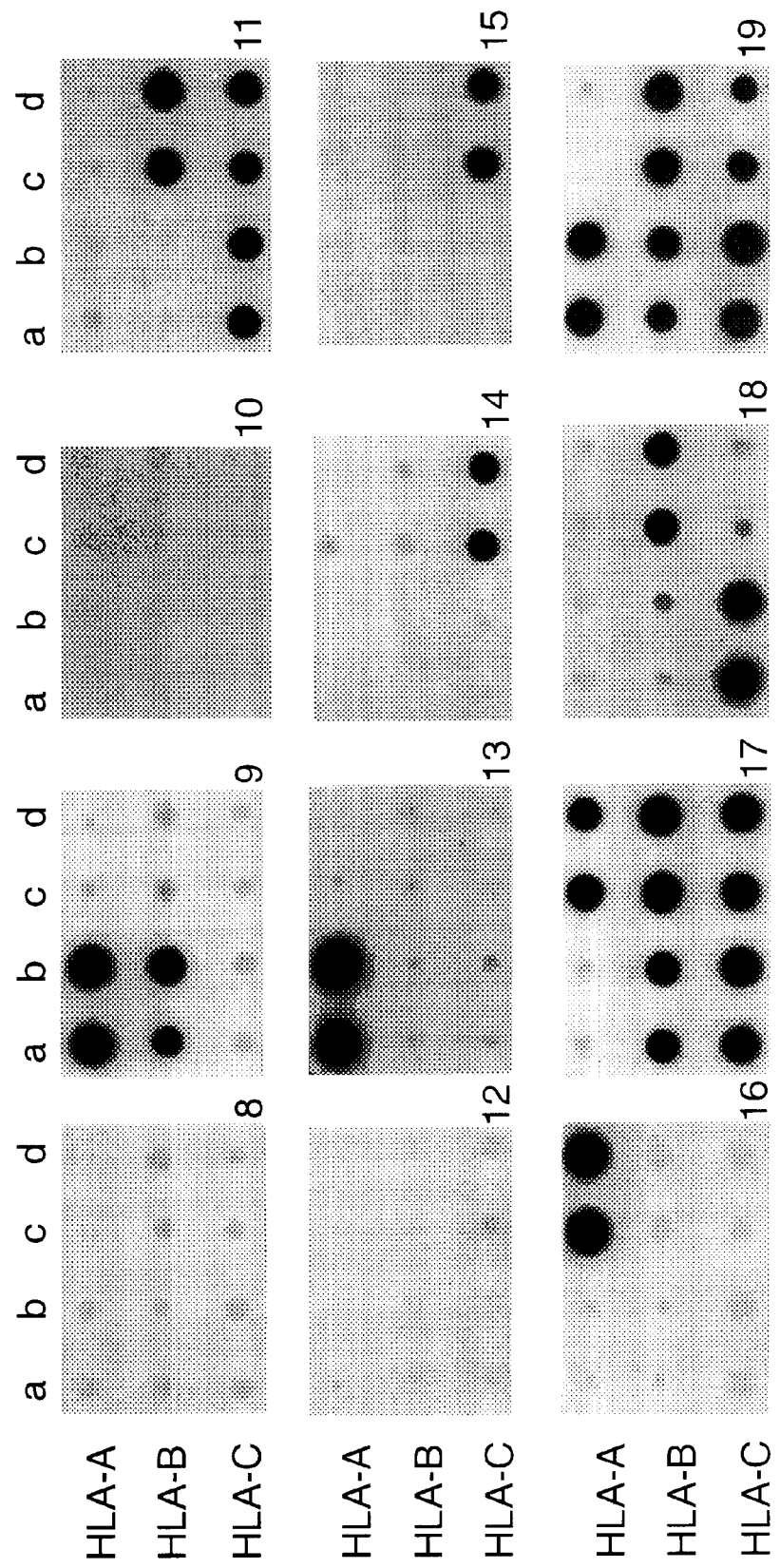

SEQUENCE LISTING

<160> NUMBER OF SEQ ID NOS: 46

<210> SEQ ID NO 1
<211> LENGTH: 18
<212> TYPE: DNA
<213> ORGANISM: Homo sapiens

<400> SEQUENCE: 1
gggccggccg cggggagc                                              18

<210> SEQ ID NO 2
<211> LENGTH: 18
<212> TYPE: DNA
<213> ORGANISM: Homo sapiens

<400> SEQUENCE: 2
ctcacagatt gaccgagt                                              18

<210> SEQ ID NO 3
<211> LENGTH: 18
<212> TYPE: DNA
<213> ORGANISM: Homo sapiens

<400> SEQUENCE: 3
cggatcgcgc tccgctac                                              18

<210> SEQ ID NO 4
<211> LENGTH: 18
<212> TYPE: DNA
<213> ORGANISM: Homo sapiens

<400> SEQUENCE: 4
tacctggagg gcctgtgc                                              18

<210> SEQ ID NO 5
<211> LENGTH: 18
<212> TYPE: DNA
<213> ORGANISM: Homo sapiens

<400> SEQUENCE: 5
cagaggatgt atggctgc                                              18

<210> SEQ ID NO 6
<211> LENGTH: 18
<212> TYPE: DNA
<213> ORGANISM: Homo sapiens

<400> SEQUENCE: 6
acaccctcca gaggatgt                                              18

<210> SEQ ID NO 7
<211> LENGTH: 18
<212> TYPE: DNA
<213> ORGANISM: Homo sapiens

<400> SEQUENCE: 7
cagaggatgt ttggctgc                                              18

<210> SEQ ID NO 8
<211> LENGTH: 18
<212> TYPE: DNA
<213> ORGANISM: Homo sapiens

```
<400> SEQUENCE: 8
cgacgtgggg ccggacgg                                                18

<210> SEQ ID NO 9
<211> LENGTH: 18
<212> TYPE: DNA
<213> ORGANISM: Homo sapiens

<400> SEQUENCE: 9
ctcacatcat ccagagga                                                18

<210> SEQ ID NO 10
<211> LENGTH: 18
<212> TYPE: DNA
<213> ORGANISM: Homo sapiens

<400> SEQUENCE: 10
tgtatggctg cgacctgg                                                18

<210> SEQ ID NO 11
<211> LENGTH: 18
<212> TYPE: DNA
<213> ORGANISM: Homo sapiens

<400> SEQUENCE: 11
ccagcaggac gcttacga                                                18

<210> SEQ ID NO 12
<211> LENGTH: 18
<212> TYPE: DNA
<213> ORGANISM: Homo sapiens

<400> SEQUENCE: 12
gtgcgtggac gggctccg                                                18

<210> SEQ ID NO 13
<211> LENGTH: 18
<212> TYPE: DNA
<213> ORGANISM: Homo sapiens

<400> SEQUENCE: 13
gcggacacgg cggctcag                                                18

<210> SEQ ID NO 14
<211> LENGTH: 18
<212> TYPE: DNA
<213> ORGANISM: Homo sapiens

<400> SEQUENCE: 14
ggagcagtgg agagccta                                                18

<210> SEQ ID NO 15
<211> LENGTH: 18
<212> TYPE: DNA
<213> ORGANISM: Homo sapiens

<400> SEQUENCE: 15
ggagcagttg agagccta                                                18

<210> SEQ ID NO 16
<211> LENGTH: 18
<212> TYPE: DNA
```

-continued

```
<213> ORGANISM: Homo sapiens

<400> SEQUENCE: 16
gtgcgtggag tggctccg                                                 18

<210> SEQ ID NO 17
<211> LENGTH: 18
<212> TYPE: DNA
<213> ORGANISM: Homo sapiens

<400> SEQUENCE: 17
ggagcagctg agagccta                                                 18

<210> SEQ ID NO 18
<211> LENGTH: 18
<212> TYPE: DNA
<213> ORGANISM: Homo sapiens

<400> SEQUENCE: 18
aggggccgga gtattggg                                                 18

<210> SEQ ID NO 19
<211> LENGTH: 18
<212> TYPE: DNA
<213> ORGANISM: Homo sapiens

<400> SEQUENCE: 19
ggcccgacgg gcgcctcc                                                 18

<210> SEQ ID NO 20
<211> LENGTH: 18
<212> TYPE: DNA
<213> ORGANISM: Homo sapiens

<400> SEQUENCE: 20
tccgcgggca taaccagt                                                 18

<210> SEQ ID NO 21
<211> LENGTH: 18
<212> TYPE: DNA
<213> ORGANISM: Homo sapiens

<400> SEQUENCE: 21
accagttcgc ctacgacg                                                 18

<210> SEQ ID NO 22
<211> LENGTH: 18
<212> TYPE: DNA
<213> ORGANISM: Homo sapiens

<400> SEQUENCE: 22
attgggaccg gaacacac                                                 18

<210> SEQ ID NO 23
<211> LENGTH: 18
<212> TYPE: DNA
<213> ORGANISM: Homo sapiens

<400> SEQUENCE: 23
tacctggagg gcacgtgc                                                 18

<210> SEQ ID NO 24
<211> LENGTH: 18
```

-continued

```
<212> TYPE: DNA
<213> ORGANISM: Homo sapiens

<400> SEQUENCE: 24
tgtatggctg cgacgtgg                                                 18

<210> SEQ ID NO 25
<211> LENGTH: 18
<212> TYPE: DNA
<213> ORGANISM: Homo sapiens

<400> SEQUENCE: 25
gcccagtcac agactgac                                                 18

<210> SEQ ID NO 26
<211> LENGTH: 18
<212> TYPE: DNA
<213> ORGANISM: Homo sapiens

<400> SEQUENCE: 26
accgagtgga cctgggga                                                 18

<210> SEQ ID NO 27
<211> LENGTH: 18
<212> TYPE: DNA
<213> ORGANISM: Homo sapiens

<400> SEQUENCE: 27
cggaacctgc gcggctac                                                 18

<210> SEQ ID NO 28
<211> LENGTH: 18
<212> TYPE: DNA
<213> ORGANISM: Homo sapiens

<400> SEQUENCE: 28
atttctacac ctccgtgt                                                 18

<210> SEQ ID NO 29
<211> LENGTH: 18
<212> TYPE: DNA
<213> ORGANISM: Homo sapiens

<400> SEQUENCE: 29
gcccgtgtgg cggagcag                                                 18

<210> SEQ ID NO 30
<211> LENGTH: 18
<212> TYPE: DNA
<213> ORGANISM: Homo sapiens

<400> SEQUENCE: 30
gatctccaag accaacac                                                 18

<210> SEQ ID NO 31
<211> LENGTH: 18
<212> TYPE: DNA
<213> ORGANISM: Homo sapiens

<400> SEQUENCE: 31
tgaccagtcc gcctacga                                                 18

<210> SEQ ID NO 32
```

```
<211> LENGTH: 18
<212> TYPE: DNA
<213> ORGANISM: Homo sapiens

<400> SEQUENCE: 32
aacacacaga tctacaag                                                 18

<210> SEQ ID NO 33
<211> LENGTH: 18
<212> TYPE: DNA
<213> ORGANISM: Homo sapiens

<400> SEQUENCE: 33
cgcgggcgcc gtgggtgg                                                 18

<210> SEQ ID NO 34
<211> LENGTH: 18
<212> TYPE: DNA
<213> ORGANISM: Homo sapiens

<400> SEQUENCE: 34
agatacctgg agaacggg                                                 18

<210> SEQ ID NO 35
<211> LENGTH: 15
<212> TYPE: DNA
<213> ORGANISM: Homo sapiens

<400> SEQUENCE: 35
tctcacaccc tccag                                                    15

<210> SEQ ID NO 36
<211> LENGTH: 19
<212> TYPE: DNA
<213> ORGANISM: Homo sapiens

<400> SEQUENCE: 36
accaacacac agactgacc                                                19

<210> SEQ ID NO 37
<211> LENGTH: 16
<212> TYPE: DNA
<213> ORGANISM: Homo sapiens

<400> SEQUENCE: 37
ggcggagcag cggaga                                                   16

<210> SEQ ID NO 38
<211> LENGTH: 18
<212> TYPE: DNA
<213> ORGANISM: Homo sapiens

<400> SEQUENCE: 38
caggacgcct acgacggc                                                 18

<210> SEQ ID NO 39
<211> LENGTH: 18
<212> TYPE: DNA
<213> ORGANISM: Homo sapiens

<400> SEQUENCE: 39
gaggacctgc gctcctgg                                                 18
```

```
<210> SEQ ID NO 40
<211> LENGTH: 18
<212> TYPE: DNA
<213> ORGANISM: Homo sapiens

<400> SEQUENCE: 40
gaaggagacg ctgcagcg                                              18

<210> SEQ ID NO 41
<211> LENGTH: 26
<212> TYPE: DNA
<213> ORGANISM: Homo sapiens

<400> SEQUENCE: 41
gaaacsgcct ctgygggag aagcaa                                      26

<210> SEQ ID NO 42
<211> LENGTH: 24
<212> TYPE: DNA
<213> ORGANISM: Homo sapiens

<400> SEQUENCE: 42
ctcccctctg ttaaccctgg ttgt                                       24

<210> SEQ ID NO 43
<211> LENGTH: 22
<212> TYPE: DNA
<213> ORGANISM: Homo sapiens

<400> SEQUENCE: 43
gggaggagcg aggggaccsc ag                                         22

<210> SEQ ID NO 44
<211> LENGTH: 23
<212> TYPE: DNA
<213> ORGANISM: Homo sapiens

<400> SEQUENCE: 44
tatccagcgg cccctaccgg agg                                        23

<210> SEQ ID NO 45
<211> LENGTH: 21
<212> TYPE: DNA
<213> ORGANISM: Homo sapiens

<400> SEQUENCE: 45
agcgaggkgc ccgcccggcg a                                          21

<210> SEQ ID NO 46
<211> LENGTH: 23
<212> TYPE: DNA
<213> ORGANISM: Homo sapiens

<400> SEQUENCE: 46
tcaccnctcg gaagggtag agg                                         23
```

METHOD FOR IDENTIFYING AN UNKNOWN ALLELE

The invention relates to a method and a kit for identifying an unknown allele of a polyallelic gene.

1. BACKGROUND TO THE INVENTION
1.1 General Introduction

Many genes exist an multiple alleles which differ from each other by small differences in sequence. It is sometimes desirable to identify an unknown allele of a polyallelic gene. For example, such identification is often necessary to match the alleles of the human leucocyte antigen (HLA) genes in a prospective donor and a prospective recipient in a tissue or organ transplant operation; if the donor and recipient have the same HLA alleles, the probability of the recipient rejecting the donor's tissue is greatly reduced.

However, it can be a difficult task to identify precisely an unknown allele of a polyallelic gene because two alleles can differ from each other by as little as one nucleotide.

The difficulties are increased in genes which have a very large number of different alleles, such as the major histocompatibility complex (MHC) genes (e.g. the HLA class I genes which have 222 known alleles).

Up to date the most favourable bone marrow transplant (BMT) and kidney transplant results have been obtained using sibling donors who are genotypically HU-identical to the recipient but such donors are available for only about 30% of patients [1-5]. BMT using unrelated donor s can be successful, but theme transplants have higher rates of graft failure, increased incidence and severity of Graft versus Host Disease and more frequent complications related to delayed or inadequate immune reconstitution [4].

New molecular biological methods for detection of genetic polymorphism currently provide an opportunity to improve matching of unrelated donors as well as a research tool to investigate the relationship between genetic disparity and transplant complications. These molecular typing methods include sequence-specific amplification, hybridisation with oligonucleotide probes, heteroduplex analysis, single strand conformation polymorphism analysis and direct nucleotide sequencing.

Each of these molecular approaches has been used for routine HLA class II typing [6], but a variety of reasons related to the HLA class I gene structure has complicated and made relatively unsuccessful their application to class I typing. The reasons for these complications are the extensive polymorphism of class I and the degree of sequence homology between the A, B and C loci of class I. In addition, sequence homology between class I classical and non-classical genes and the reported 12 pseudo genes can cause problems for specific locus amplifications [7].

The low occurrence of "allele specific" sequences at polymorphic sites is a feature of the HLA class I genes. that has limited the resolution of all current DNA typing approaches. An "allele specific" sequence is a sequence that is only present in one allele and can therefore be used to distinguish the allele from other alleles. The occurrence on more than one exon of the specific sites for determining the allelic specificity causes additional problems in the identification of individual alleles. As a result, there is at present no single method of typing which can identify all HLA class I alleles of high resolution; see Table A below.

TABLE A

Comparison of some of the currently used DNA typing methods for HLA class I alleles

| Method | Reference | HLA focus | Reagents | Resolution |
|---|---|---|---|---|
| SSO | Date et al '96 Tissue Antigens 47:93–101 | A | 91 probes | High |
| SSO | Fernandez-Villa '95 Tissue Antigens 45:153–168 | B | 99 | Medium-high |
| SSO | Levine/Yang '94 Tissue Antigens 44:174–183 | Cw | 64 probes | Medium-high |
| SSP | Bunce et al '95 Tissue Antigens 46:355–367 | A, B, Cw | 104 primer mixes | Low ($\geq$serology) |
| SSP | Bunce/Welsh '94 Tissue Antigens 43:7–17 | Cw | 22 primer mixes | Low (=serology) |
| SSP | Krausa et al '93 Tissue Antigens 42:91–99 | A9, 10, 19, 28 | 30 primer mixes | Medium |
| SSP (nested) | Krausa et al '95 Tissue Antigens 45:223–231 | A2 | 15 primer mixes | High |
| PCR-RFLP | Tatari et al '95 ProcNatlAcadSci 92:8803–7 | Cw (partial, 23) | 3 primer pairs, 11 endonucleases | High |
| SSP-SEQUENCING | Blasczyk et al '95 Tissue Antigens 46:86–95 | A (40 alleles) | 27 primer pairs automatic sequencing with fluorescent tracers | High |
| SSP-SEQUENCING | Petersdorf/Hansen '95 Tissue Antigens 46:73–85 | B (98 alleles) | 5 primer pairs automatic sequencing with fluourescent tracers | Medium-high |
| URSTO | Arguello et al '96 ProcNatlAcadSci 9 3:10961–5 | A, B, Cw (201 alleles) | 3 primer pairs 40 probes | High |

Methods For Allele Separation
1.2 Sequence Specific Primer Amplification (PCR-SSP)

This method utilises both the group-specific and, when present, allele-specific sequence sites in PCR primer design. The SSP design is based on the amplification refractory mutation system (ARMS), in which a mismatch at the 3' residue of the primer inhibits non-specific amplification [8,9].

Although each SSP reaction may not individually provide sufficient specificity to define an allele, the use of combinations of sequence specific primers allows the amplification of their common sequences to give the desired specificity.

However, despite its high accuracy, PCR-SSP is only in some cases more informative than serology. The reason for this is the low occurrence of allele specific sequence motifs in the exons and this limitation has stimulated a vast amount of research into the identification of allele specific motifs even in the intron sequences [10]. However, up to date this approach has not contributed considerably to the identification of more alleles.

Another limitation of this method is that it detects a limited number of polymorphic sequences which are utilised to predict the entire sequence. If an unknown allele is present in a particular sample this extrapolation may be incorrect.

In addition, the successful use of the technique relies on group specific amplification and therefore prior knowledge of broad HLA specificity is needed.

1.3 Single Strand Conformation Polymorphism (SSCP)

This technique is based on the electrophoretic mobility of single stranded nucleic acids in a non-denaturing polyacrylamide gel, which depends mainly on sequence-related conformation [11-13]. The technique can be employed for isolating single alleles which could then be used for further manipulation and analysis such as direct sequencing. The pattern of bands obtained after electrophoresis may be diagnostic for an allele [14,15].

The major disadvantage of SSCP is the tendency of DNA single strand to adopt many conformational forms under the same electrophoretic conditions resulting in the presence of several bands from the same product; this makes the identification more difficult. In addition there is a high degree of variation and inconsistency in the sensitivity of this method for detecting mutations or allelic variations and there is a physical limitation in the size of the DNA fragment which is of the order of 200–400 base pairs (16).

1.4 Denaturing Gradient Gel Electrophoresis (DGGE) and Temperature Gradient Gel Electrophoresis (TGGE) (17.18)

The underlying principle of both techniques is the difference in the degree of melting between two alleles (double stranded DNA) which results in a reduction of mobility of the DNA fragments in polyacrylamide gels containing a denaturing reagent (DGGE) or a temperature gradient (TGGE).

Both techniques have been used frequently for screening mutations in genetic systems with one or two variants. They are only rarely used for the separation of alleles in highly polymorphic systems such as HLA.

Both techniques require specific conditions for a particular system under investigation and, in addition, where two alleles share common sequence segments with low melting points they may not always be differentiated. The simultaneous melting of both alleles will produce very similar retardations.

1.5. Cloning of DNA

This is the classical method of preparation of a single sequence, i.e. the sequence derived from a single allele. A variety of constructs has been used to introduce the required DNA fragment into a plasmid and grow sufficient copies for analysis. This method yields pure samples of the analyte, but is time consuming to perform and several clones are normally tested to ascertain the homogeneity of the product.

Methods for the Identification of Alleles

1.6 Heteroduplex Analysis

Fully matched DNA duplexes are more stable than those with base mismatches. Instability of the duplex increases with the number of nucleotide mismatches; these cause formation of loops and bends in the linear DNA fragment which produce an increasing "drag effect" in polyacrylamide gels which retard the affected migrating bands [18-21].

Mismatched DNA hybrids (heteroduplex) may be formed at the end of each PCR cycle between coamplified alleles from a particular locus or loci due to primer cross reaction at sites with similar sequences. During the annealing stage of each cycle of the PCR, a proportion of sense strands of each allele may anneal to anti-sense strands of different alleles. The banding pattern obtained in PAGE analysis can be useful for identifying the alleles involved in the reaction [22-24].

Heteroduplex analysis is an approach that has been Utilised to compare HLA genes of a particular donor and recipient. HLA genes are amplified, denatured (melted into single strands) and mixed together under conditions that promote renaturation to form double stranded molecules. If the HLA genes of a donor and recipient are similar but not identical, heteroduplexes will form consisting of one strand of an allele of donor origin and a second strand from a different allele of recipient origin [25,26]. The sensitivity of this method can be increased by adding DNA from an HLA allele that is not present in the donor or recipient.

The major advantage of heteroduplex analysis is that it is relatively easy and inexpensive. Limitations of this approach include inability to detect certain HLA disparities, potential detection of irrelevant silent mutations and lack of specific information regarding the nature of the alleles involved.

Up to date this approach has been used for HLA class II typing with limited success. Its application to class I typing has not been successful.

1.7 Sequence Specific Oligonucleotide Probes (PCR-SSO)

SSO typing involves amplification of HLA alleles from a particular locus followed by hybridisation with a panel of oligonucleotide probes to detect polymorphic sequences that distinguish one allele or group of alleles from all others. In polymorphic systems a one step operation may not always differentiate all the known alleles; selected primers can be used to achieve amplification of individual alleles which are then identified by specific probes. This second stage of oligotyping is often referred to as high resolution oligotyping [6].

The advantages of the PCR-SSO method are specificity, sensitivity, simplicity, reproducibility, and it is relatively inexpensive to operate and allows simultaneous processing of many samples. This approach has been applied successfully, for example to typing of HLA class II alleles.

The major methodological drawback of this approach is that the complexity of the technique is directly related to the number of alleles under investigation and the presence of two alleles in the heterozygous condition can complicate the identification process.

Published oligotyping methods could result in incorrect interpretation of data if certain combinations of recently discovered alleles are present in a specimen. It is therefore necessary to update the reagents used in the identification step.

Several typing approaches for HLA-A and B based on PCR-SSO have been published; these typically require over 40 and 90 probes respectively [27,28]. The operation of these methods is time consuming and the resolution obtained is only moderate.

1.8 Nucleotide Sequencing

DNA templates for sequencing can be produced by a variety of methods, the most popular being the sequencing of cloned genomic or cDNA fragments, or the direct sequencing of DNA fragments produced solely by PCR (as in 1.2 above). These templates represent a single sequence derived from one haplotype. Alleles from both haplotypes of a heterozygous sample may be co-amplified and sequenced together using locus-specific PCR primer.

The recent availability of computer software, which allows the user to align the derived sequence against established sequence libraries, has facilitated the analysis and allele assignments for heterozygous samples in which both templates are sequenced at the same time [27]. The effectiveness of this method depends on the amount and frequency of ambiguous heterozygous combinations; for example there are many HLA class II alleles that when present together in one sample cannot be differentiated by this method. The number of such ambiguous combinations of allele sequences is even greater for HLA class I alleles.

not be distinguished on the basis of nucleotide sequences in exons 2, 3 and 4. However, if the comparison is restricted to exons 2 and 3 this number only increases to 5 pairs of ambiguous sequences. By contrast, when comparison is restricted to either exon 2 or exon 3 alone then the number of ambiguous pairs increases significantly (Table B). This observation is relevant to the design of DNA-based methods for class I typing because it shows that for practical purposes all alleles can be discriminated on the basis of sequence analysis of exon 2 and 3. Although there is some polymorphism in exon 4 encoding the α3 domain, mostly in HLA-A alleles, incorporating the information from exon 4 into the above analysis does not significantly increase the number of pairs for which the alleles can be discriminated.

TABLE B

Discriminating HLA-A, B, C alleles on the basis of partial sequences

| | | Pairs without | | | | |
|---|---|---|---|---|---|---|
| | Number of pairs | Exon 2, 3 or 4 differ. | Exon 2 or 3 differences | Exon 2 differ. | Exon 3 differ. | Exon 4 differ. |
| HLA-AXHLA-A | 1081 | 0 | 1 | 26 | 28 | 129 |
| HLA-BXHLA-B | 4851 | 2 | 3 | 117 | 89 | 880 |
| HLA-CXHLA-C | 528 | 0 | 1 | 12 | 7 | 61 |

P. Parham (7)

Up to date two HLA class I typing approaches based on direct sequencing have been published. Both require serology information followed by allele specific PCR amplification and then direct sequencing [14,30]. More recent practice, however, is to amplify DNA fragments without prior knowledge of the allele groups and to use locus specific PCR amplification. Theoretically these approaches should give the highest resolution, but they are beset by ambiguous sequence combinations which cannot be resolved satisfactorily and in practice these methods are expensive and difficult to perform routinely.

2. ANALYSIS OF THE HLA CLASS I POLYMORPHISM

Genetic recombination plays a key role in the generation of HLA alleles. This is supported by pairwise comparison of the nucleotide sequences. The most closely related pairs of alleles usually differ by localised clusters of substitutions for which both sequence motifs can be found in other alleles. This pattern implicates interallelic conversion or double recombination as the diversifying mechanism [7]. Although the vast majority of such events appear to involve recombination between alleles of the same locus, there are several cases that involve recombination between alleles of different loci [31].

In comparison to the many pairs of alleles that differ by localised clusters of substitutions, few pairs differ by point substitutions and of these only a handful differ by a substitution that has not been found in another allele. Thus, it appears that the rate at which point mutations create new alleles is slower than the rate at which new mutations are subsequently recombined with existing mutations (FIG. 1).

Comparison of allelic HLA class I sequences [32] reveals substitutions throughout the coding region. There is, however, a higher frequency of substitutions within exons 2 and 3 which encode the α1 and α2 domains of the HLA molecule. In comparing pairs of HLA-A, B and C alleles only 2 pairs out of a total of 6,460 possible combinations can In the development of PCR-based methodologies for the detection of alleles, one of the most important steps is the identification of primer sequences unique for the target gene which includes all polymorphic sites of interest in the amplified fragment, which should also be manageable in length. Typing of the polymorphic sites in exons 2 and 3 would facilitate the identification of all recognised alleles of HLA-A, B and C loci, with 5 exceptions, if suitable locus-specific amplification could be achieved.

Specificity of the primers should ensure the effective amplification of target gene fragments. In practice however, trace amplification of competing, cross-hybridising templates may also take place. In addition, due to the shared polymorphic sequence motifs between class I alleles of all three loci, non-specific coamplification of the DNA fragments would hinder specific identification. In practice, it would therefore be advantageous to use a method that allows the separation of the desired product from the undesirable PCR fragments.

Within exons 2 and 3 of the HLA-A, B and C genes there are only a few locus specific sites which are located primarily in the central region of each exon which would restrict the amplification to incomplete exon fragments. As discussed above, this would reduce the allele specific information necessary for the identification of all allelic variants.

The two polymorphic exons are flanked by introns 1 and 3, and separated by intron 2. Thus, the ideal location for primer sites to amplify exons 2 and 3 together as one fragment would be within introns 1 and 3.

Cereb and collaborators [33] have described primer sequences located in the first and third introns which can be used for locus-specific amplification of the entire exon 2 and 3 region of the HLA-A, B and C genes in one fragment. Their data indicated that the primers used in that study were effective in the amplification of HLA-A, B and C genes. Furthermore, the amplification was truly locus-specific, as assessed by hybridisation with locus-specific, group-specific, and allele-specific oligonucleotide probes.

3. SUMMARY OF THE INVENTION

The invention provides a method for identifying an unknown allele of a polyallelic gene, which method comprises (i) contacting the unknown allele with a panel of probes, each of which recognises a sequence motif that is present in some alleles of the polyallelic gene but not in others;

(ii) observing which probes recognise the unknown allele so as to obtain a fingerprint of the unknown allele; and (iii) comparing the fingerprint with fingerprints of known alleles.

The invention also provides a kit for identifying an unknown allele of a polyallelic gene, which kit comprises a panel of probes, each of which probes recognises a sequence motif that is present in some alleles of the polyallelic gene but not in others. (The same motifs may also occur in other loci in linked gene complexes with similar exon/intron structures.) The kit preferably also comprises a database which indicates which probes in the panel recognise each allele of the polyallelic gene.

The use of a panel of probes which each recognises a different motif allows identification of which motifs are present in the unknown allele. The alleles of the polyallelic gene (and alleles of other genes in a linked complex) each have a unique combination of motifs and so identification of this combination (or "fingerprint") leads to identification of the unknown alleles. Thus, the invention allows identification of alleles of polyallelic genes, such as the HLA class I genes, which may not contain "alleles specific" sequences (i.e., individual sequences which are unique to one particular allele). The technology of the invention is referred to as Universal Recombinant Site Targeting Oligonucleotide, or URSTO.

4. BRIEF DESCRIPTION OF THE DRAWINGS

FIG. 1 is a schematic representation of a polyallelic gene which has evolved by recombination events and to which the invention can be applied. See the Detailed Description of the Invention for more details.

Figure 2B:
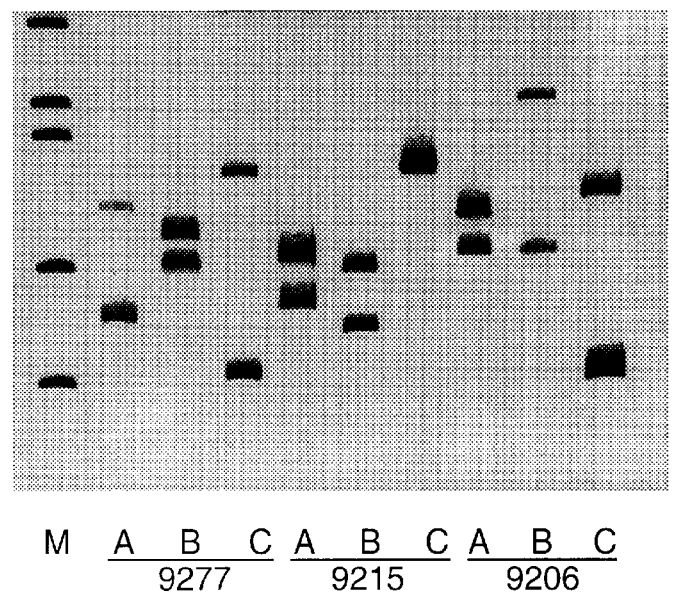
FIG. 2A shows a schematic overview of an embodiment of the "complementary Strands Analysis" (CSA) technique that can be used to purify an allele for use in the method of the invention.

FIG. 2B shows results of this CSA technique. In particular, FIG. 2B shows an autoradiograph of the separation of HLA-A,B and Cw alleles from three International Histocompatibility Workshop cell lines by PAGE. Individual bands are eluted from the gel and used for subsequent analysis. Each band is a purified product from a single allele.

Figure 3:
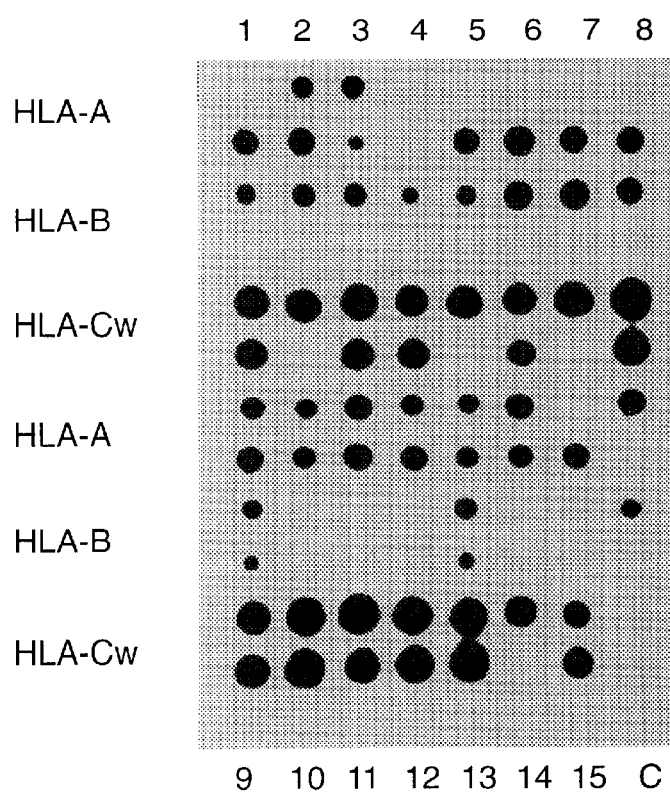

FIG. 3 shows the hybridisation pattern of an URSTO probe (number 37 from Table 1) with HLA-A, B and C allele products. DNA from 15 IHW cell lines was processed by complementary strand analysis into allelic products. These were blotted on nylon membranes and was hybridised with URSTO probes (here 37). After washing the dots were developed and chemiluminescence were captured by autoradiography. In every case the presence of a signal corresponds with the hybridization patterns described in Table 2. The unique aspect of this method is that the alleles of the three loci can be identified simultaneously by the analysis of the 40 membranes. 1–15 cell lines, C control DNA product.

FIG. 4 shows an HLA class I analysis of four cell lines with 12 URSTO probes.

HLA types of the cell lines:
a. L0541265 A*0101, B*0801, Cw*0701;
b. STIELIN A*0101, B*0801, Cw0701
c. LBUF A*3001, B*1302, Cw0602
d. BER A*0201, B*1302, Cw*0602

HLA-A, B and Cw alleles are blotted on the same membrane each membrane is hybridised with one probe. Locus specific amplification and allelic separation of the amplified fragments were performed as described in the Example below. DNA was applied to nylon membranes and these were hybridised with URSTO probes, and after washing the chemiluminescence was recorded by autoradiography.

5. DETAILED DESCRIPTION OF THE INVENTION

The invention can be applied to any polyallelic gene system in which there are motifs that are present in some alleles but not in others. The invention is mainly applicable to polyallelic systems that have evolved by recombination events and/or by gene conversion in polygenic linked complexes. Examples of genes to which the invention can be applied are the mammalian MHC genes (e.g. the HLA class I and class II genes), the T cell receptor genes in mammals [36,37], TAP, LMP, ras, nonclassical HLA class I genes, human complement factor genes C4 and C2, Bf in the HLA complex, and genes located in mitochondrial DNA, bacterial chromosomes and viral DNA.

FIG. 1 illustrates a motif pattern that could have evolved from two alleles, each with four motifs (rectangles), of an ancestral gene. There are also allele specific sequences on each allele (diamond shape) which may have evolved from point mutations. The allele specific sequences are targets for SSO and SSP type allele identification techniques, but a minimum of 13 probes would be needed. In the method of the invention, only four. probes (indicated on the top of the Figure) would be required to type the entire range. New coherent patterns would indicate new unknown alleles as shown at the foot of the Figure.

Identification of the alleles is by the presence or absence of hybridisation (+or – respectively) of the probes as shown in FIG. 3. Lack of binding, i.e. "–" in this system, is an important signal for pattern formation. No pattern is repeated in this 16 allele system and therefore each of the 16 alleles can be unambiguously identified by the invention.

The invention is particularly applicable to HLA class I genes. Comparison of HLA-A, B, C allelic sequences reveals a patchwork pattern in which an individual allele comprises a unique combination of sequence motifs, each of which is shared with other alleles, and only a few alleles have a specific sequence that is not present in other alleles (see Arnett and Parham (1995) Tissue Antigens 45 217–257). Many authors agree that this characteristic of the HLA class I genes has limited the resolution of all current DNA typing approaches. This feature itself has been exploited to facilitate the identification of all known class I alleles.

Comparison of the sequences of all known HLA class I alleles has led to the realisation that certain sequence motifs with one or more base substitutions recur in the same position in a locus and also in the same position in another locus. Each allele contains a unique combination of these motifs; this feature is universal in all polyallelic genes that have evolved mainly through recombination events and/or by gene conversion. It is therefore possible to identify the alleles of such genes by a limited number of selected recurring motifs.

Analysis of these common motifs in the HLA class I complex on human chromosome 6 has led to the conclusion that by selecting a limited number of motifs it would be possible to identify all known alleles of this system by unique hybridisation patterns from this selected panel. Table 1 gives examples of sense probe sequences that identify these motifs. The probes could equally well have the antisense sequences.

In essence therefore this method differs from any other hitherto described method in that it does not target allele specific regions of the gene (cf SSO and SSP) but utilises recurring motifs which in specific combinations are unique for each allele.

A very large number of allele specific motif patterns can be generated with probes. The number of motif patterns generated by these oligonucleotides are sufficient to identify at least 201 HLA class I alleles. The sequences of 40 oligonucleotides are given in Table 1 and the expected patterns shown in Table 2. Table 3 shows the location and distribution of the 40 probes in HLA class I genes.

The selection of the target motifs for these probes ensures that for a coherent pattern no two probes for the same sequence location can hybridise with the product from a single allele. Incoherent patterns indicate an error in the amplification or separation stages.

For unambiguous pattern identification it is usually necessary to analyse the alleles individually. The use of Complementary Strands Analysis (see below) is provided as a means of separating amplified alleles from each other.

TABLE 1

Nucleotide sequences and the sites of URSTO probes for the HLA class I genes

| ID NO. | Sequence | Location |
|---|---|---|
| 1 | GGG CCG GCC GCG GGG AGC | 113–130 |
| 2 | CTC ACA GAT TGA CCG AGT | 282–299 |
| 3 | CGG ATC GCG CTC CGC TAC | 307–324 |
| 4 | TAC CTG GAG GGC CTG TGC | 547–564 |
| 5 | CAG AGG ATG TAT GGC TGC | 358–375 |
| 6 | ACA CCC TCC AGA GGA TGT | 350–367 |

TABLE 1-continued

Nucleotide sequences and the sites of URSTO probes for the HLA class I genes

| ID NO. | Sequence | Location |
|---|---|---|
| 7 | CAG AGG ATG TTT GGC TGC | 358–375 |
| 8 | CGA CGT GGG GCC GGA CGG | 375–392 |
| 9 | CTC ACA TCA TCC AGA GGA | 347–364 |
| 10 | TGT ATG GCT GCG ACC TGG | 365–382 |
| 11 | CCA GCA GGA CGC TTA CGA | 411–428 |
| 12 | GTG CGT GGA CGG GCT CCG | 561–578 |
| 13 | GCG GAC ACG GCG GCT CAG | 478–495 |
| 14 | GGA GCA GTG GAG AGC CTA | 531–548 |
| 15 | GGA GCA GTT GAG AGC CTA | 531–548 |
| 16 | GTG CGT GGA GTG GCT CCG | 561–578 |
| 17 | GGA GCA GCT GAG AGC CTA | 531–548 |
| 18 | AGG GGC CGG AGT ATT GGG | 236–253 |
| 19 | GGC CCG ACG GGC GCC TCC | 382–400 |
| 20 | TCC GCG GGC ATA ACC AGT | 401–418 |
| 21 | ACC AGT TCG CCT ACG ACG | 413–430 |
| 22 | ATT GGG ACC GGA ACA CAC | 248–265 |
| 23 | TAC CTG GAG GGC ACG TGC | 557–574 |
| 24 | TGT ATG GCT GCG ACG TGG | 365–382 |
| 25 | GCC CAG TCA CAG ACT GAC | 277–292 |
| 26 | ACC GAG TGG ACC TGG GGA | 293–310 |
| 27 | CGG AAC CTG CGC GGC TAC | 307–324 |
| 28 | ATT TCT ACA CCT CCG TGT | 92–109 |
| 29 | GCC CGT GTG GCG GAG CAG | 520–537 |
| 30 | GAT CTC CAA GAC CAA CAC | 267–284 |
| 31 | TGA CCA GTC CGC CTA CGA | 411–428 |
| 32 | AAC ACA CAG ATC TAC AAG | 259–276 |
| 33 | CGC GGG CGC CGT GGG TGG | 212–229 |
| 34 | AGA TAC CTG GAG AAC GGG | 580–597 |
| 35 | TCT CAC ACC CTC CAG | 346–360 |
| 36 | ACC AAC ACA CAG ACT GAC C | 277–295 |
| 37 | GGC GGA GCA GCG GAG A | 528–543 |
| 38 | CAG GAC GCC TAC GAC GGC | 415–432 |
| 39 | GAG GAC CTG CGC TCC TGG | 454–471 |
| 40 | GAA GGA GAC GCT GCA GCG | 597–614 |

ID, identification number.

TABLE 2

Allele specific hibridisation patterns

| | | | | | | | | | | |
|---|---|---|---|---|---|---|---|---|---|---|
| A*0101 | 2 | 9 | 13 | 19 | 26 | 37 | 42 | 43 | 45 | |
| A*0102 | 9 | 13 | 19 | 26 | 37 | 42 | 43 | 45 | | |
| A*0201 | 2 | 6 | 16 | 17 | 25 | 26 | 29 | 37 | 45 | |
| A*0202 | 2 | 6 | 7 | 15 | 17 | 25 | 26 | 29 | 37 | 40 | 45 |
| A*0203 | 2 | 6 | 15 | 17 | 25 | 26 | 29 | 37 | 45 | |
| A*0204 | 2 | 16 | 17 | 25 | 26 | 29 | 37 | 45 | | |
| A*0205 | 2 | 6 | 7 | 15 | 17 | 25 | 26 | 29 | 31 | 37 | 40 | 45 |
| A*0206 | 2 | 6 | 16 | 17 | 25 | 26 | 29 | 31 | 37 | 45 |
| A*0207 | 2 | 16 | 17 | 25 | 29 | 37 | 45 | | | |
| A*0210 | 2 | 8 | 16 | 17 | 25 | 29 | 31 | 37 | 45 | |
| A*0211 | 2 | 3 | 6 | 16 | 17 | 25 | 26 | 29 | 37 | 45 |
| A*0212 | 2 | 6 | 17 | 25 | 26 | 29 | 37 | 45 | | |
| A*0213 | 2 | 6 | 17 | 25 | 26 | 29 | 37 | 45 | | |
| A*0214 | 2 | 6 | 7 | 16 | 17 | 25 | 26 | 29 | 31 | 37 | 40 | 45 |
| A*0215N | 2 | 16 | 17 | 25 | 29 | 37 | 45 | | | |
| A*0216 | 2 | 6 | 16 | 17 | 26 | 29 | 37 | 45 | | |
| A*0217 | 2 | 16 | 17 | 25 | 29 | 37 | 40 | 45 | | |
| A*0301 | 2 | 16 | 17 | 19 | 26 | 28 | 29 | 37 | 43 | 45 |
| A*0302 | 2 | 17 | 19 | 26 | 28 | 29 | 37 | 43 | 45 | |
| A*1101 | 2 | 9 | 17 | 19 | 26 | 28 | 29 | 31 | 37 | 43 | 45 |

TABLE 2-continued

| Allele | | | | | | | | | | | | | | |
|---|---|---|---|---|---|---|---|---|---|---|---|---|---|---|
| A*1102 | 9 | 17 | 19 | 26 | 28 | 29 | 31 | 37 | 43 | 45 | | | | |
| A*2301 | 2 | 4 | 13 | 16 | 19 | 25 | 32 | 37 | 40 | 45 | | | | |
| A*2402 | 2 | 4 | 13 | 19 | 25 | 37 | 40 | 45 | | | | | | |
| A*2403 | 2 | 4 | 17 | 19 | 25 | 37 | 40 | 45 | | | | | | |
| A*2404 | 2 | 13 | 19 | 25 | 37 | 40 | 45 | | | | | | | |
| A*2405 | 2 | 4 | 13 | 19 | 25 | 37 | 40 | 45 | | | | | | |
| A*2406 | 2 | 4 | 13 | 15 | 19 | 25 | 37 | 40 | 45 | | | | | |
| A*2407 | 2 | 4 | 13 | 19 | 25 | 28 | 37 | 40 | 45 | | | | | |
| A*2501 | 2 | 4 | 6 | 9 | 12 | 15 | 17 | 19 | 24 | 26 | 31 | 37 | 45 | |
| A*2601 | 2 | 6 | 9 | 12 | 15 | 17 | 19 | 24 | 26 | 31 | 37 | 45 | | |
| A*2602 | 6 | 9 | 15 | 17 | 19 | 24 | 26 | 31 | 37 | 45 | | | | |
| A*2603 | 2 | 6 | 9 | 12 | 15 | 17 | 19 | 24 | 26 | 29 | 31 | 37 | 45 | |
| A*2604 | 2 | 5 | 6 | 9 | 12 | 15 | 17 | 19 | 24 | 26 | 31 | 37 | 45 | |
| A*2605 | 2 | 6 | 9 | 12 | 15 | 17 | 19 | 24 | 26 | 31 | 37 | 45 | | |
| A*2901 | 2 | 16 | 17 | 19 | 25 | 28 | 32 | 37 | 43 | 45 | | | | |
| A*2902 | 2 | 16 | 17 | 19 | 25 | 26 | 28 | 32 | 37 | 43 | 45 | | | |
| A*3001 | 16 | 17 | 25 | 26 | 28 | 29 | 37 | 45 | | | | | | |
| A*3002 | 16 | 17 | 25 | 26 | 37 | 45 | | | | | | | | |
| A*3003 | 16 | 17 | 19 | 25 | 26 | 37 | 45 | | | | | | | |
| A*3004 | 15 | 17 | 25 | 26 | 37 | 45 | | | | | | | | |
| A*3005 | 15 | 17 | 25 | 26 | 37 | 45 | | | | | | | | |
| A*31011 | 2 | 3 | 16 | 17 | 25 | 26 | 29 | 32 | 37 | 43 | 45 | | | |
| A*31012 | 2 | 3 | 16 | 17 | 25 | 26 | 29 | 32 | 37 | 43 | 45 | | | |
| A*3201 | 2 | 4 | 9 | 16 | 17 | 19 | 25 | 26 | 32 | 37 | 43 | 45 | | |
| A*3301 | 2 | 3 | 16 | 17 | 19 | 24 | 25 | 26 | 29 | 32 | 43 | 45 | | |
| A*3302 | 3 | 16 | 17 | 19 | 24 | 25 | 26 | 29 | 32 | 37 | 43 | 45 | | |
| A*3303 | 2 | 3 | 16 | 17 | 19 | 24 | 25 | 26 | 29 | 32 | 37 | 43 | 45 | |
| A*3401 | 2 | 6 | 9 | 12 | 15 | 17 | 19 | 24 | 25 | 26 | 28 | 29 | 31 | 37 | 45 |
| A*3402 | 2 | 16 | 17 | 19 | 24 | 25 | 26 | 28 | 29 | 31 | 37 | 45 | | |
| A*3601 | 2 | 9 | 17 | 19 | 25 | 26 | 37 | 42 | 43 | 45 | | | | |
| A*4301 | 2 | 6 | 9 | 12 | 15 | 17 | 19 | 26 | 31 | 37 | 45 | | | |
| A*6601 | 2 | 6 | 9 | 12 | 15 | 17 | 19 | 24 | 26 | 28 | 29 | 31 | 37 | 45 |
| A*6602 | 2 | 6 | 9 | 12 | 15 | 17 | 19 | 24 | 26 | 28 | 29 | 31 | 37 | 45 |
| A*68011 | 2 | 15 | 17 | 19 | 24 | 25 | 26 | 28 | 29 | 31 | 37 | 43 | 45 | |
| A*68012 | 2 | 15 | 17 | 19 | 24 | 25 | 26 | 28 | 29 | 37 | 43 | 45 | | |
| A*6802 | 2 | 6 | 9 | 15 | 17 | 19 | 24 | 25 | 26 | 28 | 29 | 37 | 45 | |
| A*6901 | 2 | 6 | 16 | 17 | 19 | 24 | 25 | 26 | 28 | 29 | 31 | 37 | 45 | |
| A*7401 | 2 | 9 | 16 | 17 | 19 | 25 | 26 | 29 | 32 | 37 | 43 | 45 | | |
| A*8001 | 2 | 13 | 18 | 26 | 37 | 43 | 45 | | | | | | | |
| HLA-B alleles | | | | | | | | | | | | | | |
| B*0702 | 2 | 9 | 14 | 17 | 19 | 24 | 30 | 31 | 35 | 37 | 40 | 42 | 44 | |
| B*0703 | 2 | 9 | 14 | 17 | 19 | 24 | 30 | 31 | 35 | 37 | 40 | 41 | 42 | 44 |
| B*0704 | 2 | 9 | 14 | 17 | 19 | 24 | 30 | 31 | 35 | 37 | 40 | 44 | | |
| B*0705 | 2 | 9 | 14 | 17 | 19 | 22 | 24 | 30 | 31 | 35 | 37 | 40 | 42 | 44 |
| B*0801 | 2 | 9 | 17 | 19 | 22 | 24 | 25 | 30 | 32 | 37 | 40 | 41 | 44 | |
| B*0802 | 2 | 9 | 17 | 19 | 22 | 24 | 25 | 32 | 37 | 40 | 41 | 44 | | |
| B*1301 | 2 | 6 | 10 | 11 | 17 | 18 | 19 | 22 | 32 | 33 | 37 | 45 | | |
| B*1302 | 2 | 11 | 17 | 18 | 19 | 22 | 32 | 33 | 37 | 45 | | | | |
| B*1303 | 2 | 5 | 11 | 17 | 18 | 19 | 22 | 32 | 33 | 37 | 45 | | | |
| B*1401 | 2 | 9 | 17 | 18 | 23 | 24 | 25 | 26 | 30 | 31 | 40 | 41 | 45 | |
| B*1402 | 2 | 9 | 17 | 18 | 23 | 24 | 25 | 26 | 30 | 40 | 41 | 45 | | |
| B*1501 | 2 | 5 | 7 | 9 | 14 | 15 | 17 | 19 | 30 | 33 | 34 | 37 | 40 | 45 |
| B*1502 | 2 | 5 | 6 | 9 | 10 | 14 | 17 | 18 | 19 | 24 | 26 | 30 | 33 | 34 | 37 | 45 |
| B*1503 | 2 | 5 | 7 | 9 | 14 | 17 | 18 | 19 | 30 | 33 | 34 | 37 | 40 | 45 |
| B*1504 | 2 | 5 | 9 | 14 | 15 | 17 | 19 | 26 | 30 | 33 | 34 | 37 | 45 | |
| B*1505 | 2 | 5 | 7 | 9 | 14 | 17 | 18 | 19 | 30 | 32 | 33 | 34 | 37 | 40 | 45 |
| B*1506 | 2 | 5 | 7 | 8 | 9 | 14 | 17 | 18 | 19 | 30 | 33 | 34 | 37 | 40 | 45 |
| B*1507 | 2 | 5 | 9 | 14 | 15 | 17 | 19 | 30 | 33 | 34 | 37 | 40 | 45 | |
| B*1508 | 2 | 5 | 7 | 9 | 14 | 15 | 17 | 19 | 24 | 30 | 34 | 37 | 40 | 45 |
| B*1509 | 2 | 5 | 7 | 9 | 14 | 17 | 18 | 19 | 22 | 24 | 30 | 37 | 40 | 45 |
| B*1510 | 2 | 5 | 7 | 9 | 14 | 17 | 18 | 19 | 24 | 30 | 37 | 40 | 45 | |
| B*1511 | 2 | 5 | 7 | 9 | 14 | 15 | 17 | 19 | 24 | 30 | 34 | 35 | 37 | 40 | 45 |
| B*1512 | 2 | 5 | 7 | 9 | 13 | 14 | 15 | 19 | 30 | 33 | 34 | 37 | 40 | 45 |
| B*1513 | 2 | 4 | 5 | 6 | 9 | 10 | 14 | 17 | 18 | 19 | 24 | 26 | 33 | 34 | 37 | 45 |
| B*1514 | 2 | 5 | 7 | 9 | 14 | 15 | 19 | 30 | 33 | 34 | 37 | 40 | 45 | |
| B*1515 | 2 | 5 | 7 | 9 | 14 | 15 | 17 | 19 | 24 | 30 | 33 | 34 | 37 | 40 | 45 |
| B*1516 | 2 | 4 | 5 | 6 | 11 | 14 | 17 | 18 | 19 | 34 | 37 | 45 | | |
| B*1517 | 2 | 4 | 5 | 7 | 9 | 14 | 17 | 18 | 19 | 34 | 37 | 40 | 43 | 45 |
| B*1518 | 2 | 5 | 7 | 9 | 14 | 17 | 18 | 19 | 24 | 30 | 34 | 37 | 40 | 45 |
| B*1519 | 2 | 5 | 7 | 9 | 13 | 14 | 15 | 19 | 30 | 33 | 34 | 37 | 40 | 45 |
| B*1520 | 2 | 5 | 6 | 10 | 11 | 17 | 18 | 19 | 20 | 30 | 32 | 33 | 34 | 37 | 45 |
| B*1521 | 2 | 5 | 6 | 9 | 10 | 14 | 17 | 18 | 19 | 24 | 26 | 30 | 34 | 37 | 45 |
| B*1522 | 2 | 5 | 7 | 9 | 14 | 15 | 19 | 24 | 30 | 34 | 37 | 40 | 45 | |
| B*1523 | 2 | 4 | 5 | 7 | 9 | 14 | 17 | 18 | 19 | 24 | 34 | 37 | 40 | 45 |
| B*1524 | 2 | 4 | 5 | 7 | 9 | 14 | 15 | 17 | 19 | 23 | 34 | 37 | 40 | 45 |
| B*1525 | 2 | 5 | 6 | 9 | 10 | 14 | 17 | 18 | 19 | 26 | 30 | 33 | 34 | 37 | 45 |
| B*1526N | 2 | 5 | 7 | 9 | 14 | 15 | 17 | 19 | 30 | 33 | 34 | 37 | 40 | 45 |
| B*1528 | 2 | 5 | 7 | 9 | 14 | 15 | 17 | 19 | 30 | 33 | 34 | 37 | 40 | 45 |

TABLE 2-continued

| | | | | | | | | | | | | | | | | |
|---|---|---|---|---|---|---|---|---|---|---|---|---|---|---|---|---|
| B*1529 | 2 | 5 | 7 | 9 | 14 | 17 | 18 | 19 | 24 | 30 | 34 | 37 | 40 | 45 | | |
| B*1801 | 2 | 7 | 9 | 17 | 18 | 19 | 24 | 25 | 30 | 32 | 33 | 34 | 40 | 45 | | |
| B*1802 | 2 | 9 | 17 | 18 | 19 | 24 | 25 | 26 | 30 | 32 | 33 | 34 | 40 | 45 | | |
| B*2702 | 2 | 4 | 9 | 14 | 17 | 18 | 19 | 26 | 32 | 37 | 40 | 43 | 45 | | | |
| B*2703 | 2 | 9 | 14 | 17 | 18 | 26 | 32 | 37 | 40 | 43 | 45 | | | | | |
| B*27052 | 2 | 9 | 14 | 17 | 18 | 19 | 26 | 32 | 37 | 40 | 43 | 45 | | | | |
| B*27053 | 2 | 9 | 17 | 18 | 19 | 26 | 32 | 37 | 40 | 43 | 45 | | | | | |
| B*2706 | 2 | 9 | 14 | 17 | 18 | 19 | 26 | 37 | 40 | 45 | | | | | | |
| B*2707 | 2 | 9 | 14 | 17 | 18 | 19 | 22 | 32 | 37 | 40 | 44 | 45 | | | | |
| B*2708 | 2 | 9 | 14 | 17 | 18 | 19 | 26 | 30 | 32 | 37 | 40 | 43 | 45 | | | |
| B*2709 | 2 | 9 | 14 | 17 | 18 | 19 | 26 | 32 | 37 | 40 | 45 | | | | | |
| B*3501 | 2 | 5 | 6 | 10 | 11 | 17 | 18 | 19 | 20 | 24 | 30 | 32 | 34 | 37 | 45 | |
| B*3502 | 2 | 5 | 6 | 10 | 11 | 17 | 18 | 19 | 22 | 24 | 30 | 32 | 37 | 45 | | |
| B*3503 | 2 | 5 | 6 | 10 | 11 | 17 | 18 | 19 | 20 | 23 | 24 | 30 | 32 | 37 | 45 | |
| B*3504 | 2 | 5 | 6 | 10 | 11 | 17 | 18 | 19 | 20 | 22 | 24 | 30 | 32 | 37 | 45 | |
| B*3505 | 2 | 5 | 17 | 18 | 19 | 20 | 24 | 30 | 32 | 34 | 37 | 40 | 45 | | | |
| B*3506 | 2 | 5 | 6 | 10 | 11 | 17 | 18 | 19 | 20 | 22 | 23 | 24 | 30 | 32 | 37 | 45 |
| B*3507 | 5 | 6 | 10 | 11 | 17 | 18 | 19 | 20 | 24 | 30 | 32 | 34 | 37 | 45 | | |
| B*3508 | 2 | 5 | 6 | 10 | 11 | 17 | 19 | 20 | 24 | 30 | 32 | 34 | 37 | 42 | 45 | |
| B*3509 | 2 | 5 | 6 | 10 | 11 | 17 | 18 | 19 | 20 | 22 | 24 | 30 | 32 | 37 | 44 | 45 |
| B*3510 | 2 | 5 | 6 | 10 | 11 | 17 | 18 | 19 | 20 | 30 | 32 | 34 | 37 | 45 | | |
| B*3511 | 2 | 5 | 6 | 10 | 11 | 17 | 18 | 19 | 20 | 24 | 30 | 34 | 37 | 45 | | |
| B*3512 | 2 | 5 | 9 | 10 | 17 | 18 | 19 | 22 | 24 | 30 | 32 | 37 | 45 | | | |
| B*3513 | 2 | 5 | 6 | 10 | 11 | 17 | 18 | 19 | 20 | 23 | 30 | 32 | 37 | 45 | | |
| B*3701 | 2 | 9 | 17 | 19 | 23 | 25 | 32 | 33 | 37 | 45 | | | | | | |
| B*3801 | 2 | 4 | 7 | 9 | 17 | 22 | 23 | 24 | 25 | 31 | 32 | 37 | 40 | 45 | | |
| B*3802 | 2 | 7 | 9 | 17 | 22 | 23 | 24 | 25 | 31 | 32 | 37 | 40 | 45 | | | |
| B*39011 | 2 | 7 | 9 | 17 | 22 | 23 | 24 | 25 | 30 | 31 | 32 | 37 | 40 | 41 | 45 | |
| B*39013 | 2 | 7 | 9 | 17 | 22 | 23 | 24 | 25 | 30 | 31 | 32 | 37 | 40 | 41 | 45 | |
| B*39021 | 2 | 7 | 9 | 17 | 22 | 23 | 25 | 30 | 31 | 32 | 33 | 37 | 40 | 41 | 45 | |
| B*39022 | 2 | 7 | 9 | 17 | 19 | 22 | 23 | 25 | 30 | 31 | 32 | 33 | 37 | 40 | 41 | 45 |
| B*3903 | 2 | 9 | 17 | 22 | 23 | 24 | 25 | 30 | 31 | 32 | 37 | 40 | 41 | 45 | | |
| B*3904 | 2 | 7 | 9 | 17 | 22 | 23 | 24 | 25 | 30 | 32 | 37 | 40 | 41 | 45 | | |
| B*3905 | 2 | 7 | 9 | 17 | 22 | 23 | 24 | 25 | 30 | 31 | 32 | 37 | 40 | 45 | | |
| B*39061 | 2 | 9 | 17 | 22 | 23 | 24 | 25 | 30 | 31 | 32 | 37 | 41 | 45 | | | |
| B*39062 | 2 | 9 | 17 | 22 | 23 | 24 | 25 | 26 | 30 | 31 | 32 | 37 | 41 | 45 | | |
| B*3907 | 2 | 7 | 9 | 17 | 24 | 25 | 30 | 31 | 32 | 34 | 37 | 40 | 45 | | | |
| B*3908 | 2 | 7 | 9 | 17 | 22 | 23 | 25 | 30 | 31 | 32 | 33 | 37 | 40 | 42 | 45 | |
| B*40011 | 2 | 7 | 9 | 14 | 17 | 18 | 19 | 22 | 30 | 32 | 33 | 37 | 40 | 44 | | |
| B*40012 | 2 | 7 | 9 | 14 | 17 | 18 | 19 | 22 | 30 | 32 | 33 | 37 | 40 | 44 | | |
| B*4002 | 2 | 9 | 14 | 17 | 18 | 19 | 22 | 30 | 32 | 33 | 37 | 40 | 44 | 45 | | |
| B*4003 | 2 | 9 | 14 | 17 | 18 | 19 | 30 | 32 | 33 | 34 | 37 | 40 | 44 | 45 | | |
| B*4004 | 2 | 6 | 10 | 11 | 14 | 17 | 18 | 19 | 22 | 30 | 32 | 33 | 37 | 44 | 45 | |
| B*4005 | 2 | 5 | 9 | 14 | 17 | 18 | 19 | 22 | 30 | 32 | 37 | 40 | 44 | 45 | | |
| B*4006 | 2 | 9 | 14 | 17 | 18 | 19 | 22 | 26 | 30 | 32 | 33 | 37 | 44 | 45 | | |
| B*4007 | 2 | 7 | 9 | 14 | 17 | 18 | 19 | 22 | 30 | 32 | 37 | 40 | 44 | | | |
| B*4101 | 2 | 6 | 9 | 17 | 19 | 22 | 25 | 26 | 30 | 32 | 33 | 37 | 44 | | | |
| B*4102 | 2 | 9 | 17 | 19 | 22 | 25 | 30 | 32 | 33 | 37 | 40 | 44 | | | | |
| B*4201 | 2 | 9 | 17 | 19 | 22 | 24 | 25 | 30 | 31 | 32 | 35 | 37 | 40 | 44 | | |
| B*4402 | 2 | 5 | 9 | 10 | 19 | 32 | 33 | 37 | 43 | 45 | | | | | | |
| B*44031 | 2 | 5 | 9 | 10 | 18 | 19 | 32 | 33 | 37 | 43 | 45 | | | | | |
| B*44032 | 2 | 5 | 6 | 9 | 10 | 18 | 19 | 26 | 32 | 33 | 37 | 43 | 45 | | | |
| B*4404 | 2 | 9 | 10 | 19 | 25 | 32 | 33 | 37 | 42 | 43 | 45 | | | | | |
| B*4405 | 2 | 5 | 9 | 10 | 19 | 32 | 33 | 37 | 45 | | | | | | | |
| B*4406 | 2 | 4 | 5 | 9 | 10 | 19 | 24 | 32 | 37 | 43 | 45 | | | | | |
| B*4501 | 2 | 5 | 6 | 11 | 19 | 20 | 30 | 32 | 33 | 37 | 45 | | | | | |
| B*4601 | 2 | 5 | 7 | 9 | 14 | 15 | 17 | 19 | 30 | 34 | 37 | 45 | | | | |
| B*4701 | 2 | 7 | 8 | 9 | 14 | 17 | 18 | 19 | 32 | 33 | 37 | 40 | 43 | 45 | | |
| B*4801 | 2 | 9 | 14 | 17 | 18 | 19 | 22 | 30 | 31 | 32 | 33 | 37 | 40 | 44 | | |
| B*4802 | 2 | 5 | 6 | 10 | 11 | 17 | 18 | 19 | 20 | 30 | 31 | 32 | 33 | 34 | 37 | 45 |
| B*4901 | 2 | 4 | 5 | 6 | 11 | 17 | 18 | 19 | 20 | 33 | 37 | 45 | | | | |
| B*5001 | 2 | 5 | 6 | 11 | 17 | 18 | 19 | 20 | 30 | 33 | 37 | 45 | | | | |
| B*5101 | 2 | 4 | 5 | 9 | 17 | 18 | 19 | 22 | 24 | 26 | 45 | | | | | |
| B*5102 | 2 | 4 | 5 | 9 | 17 | 18 | 19 | 22 | 24 | 26 | 37 | 45 | | | | |
| B*5103 | 2 | 4 | 5 | 9 | 18 | 19 | 22 | 24 | 26 | 45 | | | | | | |
| B*5104 | 2 | 4 | 5 | 6 | 9 | 10 | 17 | 18 | 19 | 22 | 24 | 26 | 45 | | | |
| B*5105 | 2 | 4 | 5 | 9 | 17 | 19 | 22 | 24 | 26 | 32 | 37 | 42 | 45 | | | |
| B*52011 | 2 | 4 | 5 | 9 | 17 | 18 | 19 | 22 | 26 | 33 | 45 | | | | | |
| B*52012 | 2 | 4 | 5 | 9 | 17 | 18 | 19 | 22 | 26 | 33 | 45 | | | | | |
| B*5301 | 2 | 4 | 5 | 6 | 10 | 11 | 17 | 18 | 19 | 20 | 24 | 32 | 34 | 37 | 45 | |
| B*5401 | 2 | 11 | 17 | 18 | 19 | 22 | 24 | 25 | 30 | 32 | 35 | 36 | 37 | 45 | | |
| B*5501 | 2 | 11 | 17 | 18 | 19 | 22 | 24 | 25 | 30 | 35 | 37 | 45 | | | | |
| B*5502 | 2 | 11 | 17 | 18 | 19 | 22 | 24 | 25 | 30 | 32 | 35 | 37 | 45 | | | |
| B*5601 | 2 | 5 | 11 | 17 | 18 | 19 | 22 | 24 | 30 | 32 | 35 | 37 | 45 | | | |
| B*5602 | 2 | 5 | 7 | 17 | 18 | 19 | 22 | 24 | 30 | 32 | 35 | 37 | 40 | 45 | | |
| B*5701 | 2 | 4 | 5 | 9 | 14 | 17 | 18 | 19 | 26 | 32 | 34 | 37 | 45 | | | |
| B*5702 | 2 | 4 | 5 | 9 | 14 | 17 | 19 | 22 | 26 | 32 | 37 | 42 | 45 | | | |
| B*5703 | 2 | 4 | 5 | 9 | 14 | 17 | 18 | 19 | 22 | 26 | 32 | 37 | 45 | | | |
| B*5801 | 2 | 4 | 5 | 6 | 10 | 11 | 17 | 18 | 19 | 20 | 32 | 34 | 37 | 45 | | |

TABLE 2-continued

| | | | | | | | | | | | | | | | |
|---|---|---|---|---|---|---|---|---|---|---|---|---|---|---|---|
| B*5802 | 2 | 4 | 5 | 11 | 17 | 18 | 19 | 20 | 32 | 34 | 37 | 40 | 45 | | |
| B*5803 | 2 | 4 | 5 | 11 | 17 | 18 | 19 | 20 | 32 | 34 | 37 | 45 | | | |
| B*5901 | 2 | 4 | 11 | 17 | 18 | 19 | 22 | 24 | 25 | 32 | 37 | 45 | | | |
| B*67011 | 2 | 7 | 9 | 17 | 22 | 23 | 24 | 25 | 30 | 31 | 32 | 35 | 37 | 40 | 45 |
| B*67012 | 2 | 7 | 9 | 17 | 19 | 22 | 23 | 24 | 25 | 30 | 31 | 32 | 35 | 37 | 40 | 45 |
| B*7301 | 14 | 17 | 18 | 19 | 23 | 24 | 30 | 32 | 44 | 45 | | | | | |
| B*7801 | 2 | 5 | 9 | 17 | 18 | 19 | 22 | 24 | 26 | 30 | 41 | 45 | | | |
| B*7802 | 2 | 5 | 9 | 17 | 18 | 19 | 22 | 24 | 26 | 30 | 45 | | | | |
| B*8101 | 2 | 9 | 14 | 17 | 18 | 19 | 22 | 24 | 30 | 31 | 32 | 35 | 37 | 40 | 44 |
| HLA-C Alleles | | | | | | | | | | | | | | | |
| Cw*0101 | 17 | 19 | 20 | 25 | 30 | 36 | 37 | 40 | 42 | 44 | | | | | |
| Cw*0102 | 17 | 19 | 20 | 25 | 30 | 36 | 37 | 40 | 42 | 44 | 45 | | | | |
| Cw*0201 | 7 | 15 | 17 | 19 | 20 | 34 | 37 | 40 | 44 | | | | | | |
| Cw*02021 | 7 | 15 | 17 | 19 | 20 | 34 | 36 | 37 | 40 | 44 | 45 | | | | |
| Cw*02022 | 7 | 15 | 17 | 19 | 20 | 34 | 36 | 37 | 40 | 44 | 45 | | | | |
| Cw*0302 | 2 | 5 | 6 | 14 | 17 | 18 | 19 | 20 | 26 | 30 | 34 | 36 | 45 | | |
| Cw*0303 | 2 | 5 | 6 | 10 | 14 | 17 | 18 | 19 | 20 | 26 | 30 | 36 | 45 | | |
| Cw*0304 | 2 | 5 | 6 | 10 | 14 | 17 | 18 | 19 | 20 | 26 | 30 | 36 | 45 | | |
| Cw*0401 | 2 | 7 | 8 | 14 | 17 | 19 | 23 | 25 | 37 | 40 | 42 | 45 | | | |
| Cw*0402 | 2 | 7 | 8 | 14 | 17 | 19 | 23 | 25 | 37 | 40 | 45 | | | | |
| Cw*0501 | 6 | 7 | 11 | 19 | 20 | 21 | 23 | 25 | 36 | 37 | 40 | 42 | 44 | | |
| Cw*0602 | 11 | 14 | 15 | 17 | 19 | 20 | 25 | 34 | 37 | 40 | 44 | 45 | | | |
| Cw*0701 | 6 | 7 | 11 | 17 | 18 | 19 | 20 | 25 | 30 | 34 | 36 | 37 | 40 | 44 | 45 |
| Cw*0702 | 7 | 17 | 18 | 19 | 20 | 25 | 30 | 34 | 36 | 37 | 40 | 44 | 45 | | |
| Cw*0703 | 7 | 17 | 18 | 19 | 20 | 30 | 34 | 36 | 37 | 40 | 44 | 45 | | | |
| Cw*0704 | 6 | 11 | 17 | 19 | 20 | 23 | 25 | 30 | 37 | 44 | | | | | |
| Cw*0801 | 6 | 7 | 11 | 14 | 17 | 18 | 19 | 20 | 23 | 25 | 30 | 36 | 37 | 40 | 44 |
| Cw*0802 | 6 | 7 | 11 | 17 | 19 | 20 | 23 | 25 | 30 | 36 | 37 | 40 | 42 | 44 | |
| Cw*0803 | 6 | 7 | 11 | 14 | 17 | 18 | 19 | 20 | 23 | 25 | 30 | 36 | 40 | 44 | |
| Cw*1201 | 7 | 14 | 15 | 17 | 19 | 20 | 25 | 30 | 37 | 40 | 44 | 45 | | | |
| Cw*12021 | 7 | 14 | 15 | 17 | 19 | 20 | 25 | 30 | 34 | 36 | 37 | 40 | 44 | 45 | |
| Cw*12022 | 7 | 14 | 15 | 17 | 19 | 20 | 25 | 30 | 34 | 36 | 37 | 40 | 44 | 45 | |
| Cw*1203 | 11 | 14 | 15 | 17 | 19 | 20 | 25 | 30 | 34 | 36 | 37 | 40 | 44 | 45 | |
| Cw*1301 | 7 | 14 | 15 | 17 | 19 | 20 | 25 | 30 | 34 | 37 | 40 | 44 | 45 | | |
| Cw*1401 | 2 | 14 | 17 | 19 | 20 | 25 | 30 | 34 | 36 | 37 | 40 | 42 | | | |
| Cw*1402 | 2 | 14 | 17 | 19 | 20 | 25 | 30 | 34 | 36 | 37 | 40 | 42 | 45 | | |
| Cw*1403 | 2 | 14 | 17 | 19 | 20 | 25 | 30 | 34 | 36 | 37 | 40 | 42 | 45 | | |
| Cw*1501 | 6 | 10 | 11 | 14 | 17 | 18 | 19 | 20 | 25 | 36 | 37 | 45 | | | |
| Cw*1502 | 6 | 10 | 11 | 14 | 17 | 18 | 19 | 20 | 25 | 36 | 37 | 44 | 45 | | |
| Cw*1503 | 6 | 10 | 11 | 14 | 17 | 18 | 19 | 20 | 25 | 36 | 37 | 44 | 45 | | |
| Cw*1504 | 6 | 10 | 11 | 14 | 17 | 18 | 19 | 20 | 25 | 34 | 36 | 37 | 44 | 45 | |
| Cw*1505 | 6 | 10 | 11 | 14 | 17 | 18 | 19 | 20 | 23 | 25 | 36 | 37 | 44 | 45 | |
| Cw*1601 | 11 | 17 | 19 | 20 | 25 | 30 | 34 | 36 | 37 | 40 | 45 | | | | |
| Cw*1602 | 11 | 17 | 19 | 20 | 25 | 34 | 36 | 37 | 40 | 45 | | | | | |
| Cw*1603 | 11 | 14 | 17 | 19 | 20 | 25 | 30 | 34 | 36 | 37 | 40 | 44 | 45 | | |
| Cw*1701 | 6 | 11 | 14 | 17 | 18 | 19 | 20 | 23 | 36 | 37 | 44 | 45 | | | |

TABLE 3

The location of the target sequences for URSTO probes in HLA class I genes

| Sequence range | No. of probes | Probe Identity |
|---|---|---|
| 1. 92–109 | 1 | 31 |
| 2. 113–130 | 1 | 2 |
| 3. 212–229 | 1 | 36 |
| 4. 236–299 | 7 | 24,28,19,35,41,3,33 (a) |
| 5. 293–310 | 1 | 29 |
| 6. 307–324 | 2 | 4,30 |
| 7. 333–430 | 14 | 6,8,10,26,11,20,7,40,9 (b) 23,12,34,43,22 |
| 8. 454–471 | 1 | 44 |
| 9. 478–495 | 1 | 14 |
| 10. 520–578 | 9 | 5,25,32,15,16,13,17,18,42 (c) |
| 11. 580–597 | 1 | 37 |
| 12. 597–614 | 1 | 45 |

The probe identity numbers are same as in Table 1: a, b and c indicate the hypervariable sequence regions which are present in the three loci. The sequence range refers to the base positions in exons 2 and 3.

The panel of probes used in the invention generally consists of a sufficient number of probes to uniquely identify the majority of the alleles of the polyallelic gene. For example, the panel of probes may be selected so as to uniquely identify at least 50%, at least 75%, at least 90%, at least 95%, at least 99% or 100% of the alleles in the polyallelic system. The exact number of probes will vary depending on the gene, but is typically from 10 to 100, preferably from 20 to 70 or from 30 to 50. Each probe may recognise a sequence motif that is present in, for example, from 2 to 30, from 2 to 20, for 4 to 20 or from 6 to 16 alleles of the polyallelic gene.

When the invention is applied to the HLA class I system, the panel of probes preferably comprises from 20 to 40 probes which each recognises the motif recognised by one of the probes set out in Table 1. Each of the probes in the panel may have a sequence at least 40%, at least 60%, at least 80%, at least 90% or at least 95% identical to either (i) a sequence of one of the probes set out in Table 1 or (ii) a sequence complementary to a sequence of one of the probes set out in Table 1. A probe in the panel may have a sequence that is shifted along the HLA class I gene sequence by a certain number of nucleotides compared to a probe set out in Table 1; for example, a probe may be shifted along by from 1 to 10 nucleotides (e.g. from 1 to 5 nucleotides) in either a 5' or a 3' direction compared to a probe set out in Table 1.

The probes used in the invention may be labelled with any one of a variety of detectable labels in order to facilitate their detection. Examples of suitable labels include digoxygenin (which may be detected using an anti-digoxygenin antibody coupled to alkaline phosphatase), radiolabels, biotin (which may be detected by avidin or streptavidin conjugated to peroxidase) and fluorescent labels (e.g. fluorescein and rhodamine).

The kit according to the invention may comprise a database which indicates which probes in the panel in the kit recognise each allele of the polyallelic gene. The database may be a paper database or a computer database. The database may be compiled by examining the sequences of the allele of the polyallelic genes and noting the probes which would be expected to bind to each allele. The accuracy of a database compiled by such a technique may be verified by experimentally determining which alleles are bound by each probe in the panel. Table 2 contains a database showing which of the 40 probes in Table 1 bind specific HLA class I alleles. The kit may also contain one or more known alleles as control(s). Such controls can be used to verify that an experiment carried out using the kit has worked correctly.

It is highly desirable that the sample of allele used in the invention comprises one allele only and is not contaminated by other alleles of the same gene. The presence of two similar alleles in the sample can give confusing results and prevent conclusive identification of the alleles. Individuals are often heterozygous with respect to the alleles of a particular gene, i.e. individuals often have two different alleles of the same gene, and these alleles normally need to be separated before carrying out the invention.

In view of the fact that the difference between two alleles of a gone can be as little as one nucleotide, it is often difficult to separate the alleles from a mixture of the alleles. These difficulties are increased in genes which have a very large number of different alleles, such as the major histocompatibility complex (MHC) genes (e.g. the human leucocyte antigen (HLA) class I genes which have 222 known alleles).

A new method for separating alleles of a gene from a mixture of alleles has not been found, which is referred to herein as "Complementary Strands Analysis" (CSA). This patent application (WO 97/20070) in the name of the Anthony Nolan Bone Marrow Trust being filed on the same day as this application. The method comprises:
 (i) amplifying the alleles in the mixture of alleles;
 (ii) hybridising single strands of the amplified alleles with a complementary strand of a reference allele to form duplexes; and
 (iii) separating the duplexes.

The different alleles in the original mixture give rise to duplexes having different numbers of mismatches compared to a selected complementary reference DNA strand. This allows the duplexes to be separated by, for example, gel electrophoresis. The separated duplexes can then be analysed by the method of the invention to identify the alleles that were present in the original mixture.

A preferred form of the CSA method comprises
 (i) amplifying the mixture of alleles employing a pair of primers in which one of the primers carries a ligand, so as to produce an amplified mixture of double-stranded alleles in which one of the strands carries a ligand;
 (ii) contacting the amplified mixture of double-stranded alleles with a receptor on a solid support under conditions such that the ligand binds to the receptor;
 (iii) separating the mixture of double-stranded alleles into single-strands and removing the strands that are not bound to the support by the ligand;
 (iv) recovering the remaining strands from the support;
 (v) mixing the recovered strands with a complementary strand of a reference allele so as to form duplexes; and
 (vi) separating the duplexes.

Another form of the CSA method comprises
 (i) amplifying the alleles in the mixture employing a pair of primers in which one of the primers carries a high molecular weight molecule, so as to produce an amplified mixture of double-stranded alleles in which one of the strands carries a high molecular weight molecule;
 (ii) separating the mixture of double-stranded alleles into single strands;
 (iii) mixing the single strands with a complementary strand of a reference allele so as to form duplexes; and
 (iv) separating the duplexes.

This form of CSA overcomes the need for solid support systems by conjugating one primer of a pair of primers directly to a high molecular weight molecule (e.g. a protein). The amplified product after hybridisation can be applied directly to a separating gel. The high molecular weight conjugates are retained in the gel compared to the duplex without attachment of the high molecular weight molecule.

In yet another form of the CSA method, there is provided a method for separating an allele from a mixture of alleles, which method comprises
 (i) amplifying a single strand of each of the alleles in the mixture;
 (ii) mixing the amplified single strands with a complementary strand of a reference allele so as to form duplexes; and
 (iii) separating the duplexes.

The amplification of the single strand can be done, for example, by asymmetric PCR.

This form of CSA overcomes the need for both solid support systems and conjugation of one primer of a pair to a high molecular weight molecule. However, in the embodiment it is possible to use a primer carrying a ligand such as a hapten in order to facilitate capture of the amplified strand with a receptor such as an antibody and separation of the amplified strand from other components in the amplification mixture.

In each of the above forms of CSA, the reference allele may be provided in single-stranded form by essentially the same steps as used to provide the test alleles in single-stranded form.

The CSA method provides an improvement over prior methods for separating alleles. The advantages offered by CSA can be summarised as follows:
 (a) The method provides a high resolution between different alleles and differences of as little as one nucleotide between alleles can be detected.
 (b) The method allows Simultaneous and rapid processing of a large number of samples.
 (c) The method is comparatively inexpensive to perform, particularly when compared to prior methods which achieve a high level of resolution.
 (d) The method uses techniques that can be performed easily without recourse to complex and expensive technology.

The reference allele used in the CSA method generally has a known sequence. Further, the reference allele is usually chosen so as to have a similar allotype to an allotype that at least one of the test alleles is suspected of having. For example, it may be known that a test allele is of the HLA-A02 type from serological data, but it may not be known which of the seventeen A02 sub-types the allele is. In this case, the reference allele may be chosen to be of sub-type A0201 and the method of the present invention could then be used to determine which of the A02 sub-types the test allele is.

The reference strand may be obtained from (a) a homozygous source, (b) a heterozygous source from which individual strands are isolated by gel separation after amplification steps or (c) DNA synthesis. There are now about 500 internationally recognised cell lines which contain HLA alleles of known sub-type and these cell lines can be used as a source of reference alleles.

In the CSA method, the amplification steps may be carried out by polymerase chain reaction (PCR).

The ligand/receptor system used in the CSA method may, for example, be the biotin/streptavidin system. Direct conjugation of the primer via a linking group, such as short poly A, to the beads is an alternative. When the biotin/streptavidin system is used, one of the primers used in each of the amplification steps may be labelled with biotin, so that when the amplification reaction is carried out double-stranded DNA is produced in which one strand carries a biotin label. The double-stranded DNA may then be bound to a solid support coated with streptavidin.

The solid support used in the CSA method is typically magnetic beads. However, other supports may be used, such as the matrix of an affinity chromatography column. When the support is in the form of magnetic beads, the two strands of the amplified DNA are separated by attracting the beads to a magnet and washing the beads under conditions such that the double-stranded DNA dissociates into single-strands. The dissociation is typically performed by incubating the beads (e.g. three times) under alkaline conditions (e.g. 0.1 M or 0.15 M NaOH) at room temperature for about 5 or 10 minutes. Usually, the strand which is not bound to the support by the ligand is then discarded, although it is equally possible to retain the strand that is not bound to the support and discard the strand that is bound to the support.

The strand that remains attached to the support may be recovered from the support by incubating the support under conditions such that the ligand/receptor complex dissociates. When the biotin/streptavidin system is used, the support is typically heated to e.g. 95° C. for about 5 minutes; this ensures denaturation of the streptavidin molecule to release the biotinylated single strand which is then recovered.

At this stage, there have been provided a single-stranded unknown allele and the complementary strand of a reference allele. The two strands are then mixed together under conditions in which they hybridise to form duplexes.

Typically, the hybridisation step is performed by heating the mixture of strands at about 95° C. for about 3 min, at about 70° C. for about 5 min and then at about 65° C. for about 45 min.

Under these conditions, duplexes are formed which can subsequently be separated by gel electrophoresis (e.g. polyacrylamide gel electrophoresis). The electrophoresis may be carried out under denaturing or non-denaturing conditions. The use of denaturing conditions may enhance separation.

As an alternative separation technique to gel electrophoresis, high pressure liquid chromatography (HPLC) may be used.

In the embodiment of the CSA method in which one of the pair or primers is conjugated to a high molecular weight molecule, the molecule may be a protein such as bovine serum albumin (BSA). The molecular weight of the high molecular weight molecule is such that it causes the DNA molecule to which it is attached to be sufficiently retarded in the separation step (e.g. the electrophoresis step) to allow the DNA molecule to be separated from a duplex without a high molecular weight compound attached. For example, the molecular weight of the high molecular weight molecule may be from 10 to 200 kDa, preferably 20 to 100 kDa.

The invention may be used to match a prospective donor in a tissue or organ transplant operation with a prospective recipient. In particular, the invention may be used to identify the alleles of the prospective recipient and donor, and hence to determine whether they have compatible alleles. The prospective recipient and donor may, for example, be a prospective recipient and donor in a bone arrow or kidney transplant operation.

Other proposed uses of the invention include determination of the paternity of an individual by identifying one (or more) of his alleles to see if it is the same as a corresponding allele of a putative father. The invention may also be used in forensic medicine to determine the origin of a sample of body tissue or fluid, as a follow up technique in treatment of haematological malignancies or inherited disorders, in adoptive immunotherapy, and in identification of bacteria and viruses.

The following example illustrates the invention.

EXAMPLE

METHODS

1. —Locus Specific Amplification of HLA Class I Genes

For typing purposes, amplification of exons 2 and 3 is desirable, and the primers were therefore selected to amplify the stretch of the genome between intron I and intron 3. The localisation and nucleotide sequences of the HLA locus-specific primers used are given in the reagents section.

PCR reactions were performed in a total volume of 100 µl using 1 µg of genomic DNA and 25 pmoles of each locus-specific primer. The 3' primer was biotinylated at the 5' end. This arrangement ensures the incorporation of the biotinylated primer onto the amplified antisense DNA strand. PCR conditions are given in the following table.

| Thermocycling conditions A, B and Cw loci | | |
|---|---|---|
| 95° C. | 4 min. | 1 cycle |
| 95° C. | 30 sec. | |
| 65° C. | 50 sec. | 33 cycles |
| 72° C. | 30 sec. | |
| 72° C. | 8 min. | 1 cycle |

2. —Separation of the Amplified DNA Strands a) Removal of Non-biotinylated Strand:

Magnetic beads with covalently coupled streptavidin on the surface were added to the PCR product and incubated for 30 minutes at 43° C. In this way the amplified PCR product was immobilised by the interaction of biotin and streptavidin. After incubation, the tubes were placed against a magnet and the beads were washed with washing buffer to remove the remaining PCR reaction components.

The non-biotinylated DNA strand was then dissociated from the beads by incubation with 0.1 M NaOH at room temperature (r.t.) for 10 minutes. Following this the beads were washed to remove excess NaOH and resuspended in 50 µl of hybridisation buffer.

b) Removal of Biotinylated DNA Strand:

The bead suspension was heated at 95° C. for 5 minutes, which ensures denaturation of the streptavidin molecule to release the biotinylated amplified anti-sense single strand which was then removed and placed in a clean tube.

At this stage, the isolates contained single biotinylated DNA strands from each allele.

3. —Hybridisation with Locus Specific Reference Sense Single Strand DNA

The biotinylated anti-sense strand(s) from above were mixed with a locus specific reference sense strand, Rf A, Rf B and Rf C for HLA-A, B and C respectively (see below), and the mixture was heated at 95° C. for 3 min., incubated at 70° C. for 5 min. and then at 65° C. for 45 min. Under these conditions the sense and anti-sense strands were hybridised. The heteroduplexes formed by each allele anti-sense strand with the locus specific reference sense strand could subsequently be separated frog each other by electrophoresis in non-denaturing polyacrylamide gel.

4. —Preparation of Locus Specific Reference Sense Single Strand DNA.

DNA was extracted from three homozygous 10th IHW cell lines. The following cell lines were selected as locus specific reference DNA: STEINLIN (HLA-A*0101), SP0010 (HLA-B*4402) and STIENLIN (HLA-Cw*0701).

The PCR conditions for amplification were as above, with the exception that in each case the locus-specific 5' primer was biotinylated (5' end). The PCR products were analysed by PAGE to assess the fidelity of the amplification and in all cases a single band was obtained.

The biotinylated single sense strand was isolated as described above and its purity was tested by a heating/annealing cycle of the sample followed by agarose electrophoresis. In each case only a single band of the expected size was observed.

5. —Separation of Alleles

This step is critical for the separation of the allelic products from heterozygous subjects and from coamplified non-specific products.

The heteroduplexes formed as described in step 3 were separated from e ah o the r by electrophoresis analysis which was performed on an 8% non-denaturing polyacrylamide gel at room temperature (200 volts for 6 hours). The DNA was visualised by ethidium bromide staining and U.V. light.

The heteroduplexes from heterozygote individuals were resolved into two bands, while DNA from homozygote subjects produced a single band.

6. —Identification of HLA Class I alleles

The bands were excised from the gel from which the DNA was eluted and blotted on the same membrane for three loci. For heterozygous subjects two dots per locus were prepared. Several subject samples were blotted on each membrane. According to the number of the URSTO probes several membranes were prepared.

The oligonucleotide probes were labelled with digoxigenin (DIG) at the 3' end (Boehringer, according to specification).

Hybridisation and washing solutions contained TMACl (3M), and membranes were hybridised at 54° C. and washed at 58° C. Oligonucleotide binding was detected by chemiluminescence; anti-DIG-antibody conjugated to alkaline phosphatase and CSPD were added to membranes. After incubation the chemiluminescence was detected by X-ray films.

RESULTS

A. —Separation of Alleles by CSA

Anti-sense strands from more than 20 samples were isolated, hybridised with the HLA-A locus specific reference sense strand (STEINLIN A*0101), and analysed by 8% non-denaturing polyacrylamide gel electrophoresis. In all cases there was a good correlation between the number of bands observed and the zygosity of the sample. For example, two bands were seen for heterozygous samples whereas one band was seen for homozygous samples. These bands were always observed in the same area of the gel, the lower half nearest to the anode. A representative autoradiograph from CSA analysis is presented in FIG. 2B.

B. —Identification of Alleles by URSTO

For initial testing of the labelled URSTO probes, DNA from 10 homozygous EBV transformed B cell lines set out in the following table was amplified for the HLA-A, B and C loci using locus specific primers and blotted onto 10 nylon membranes.

| Specificity of the 10 homozygous cell lines used in URSTO | | | |
|---|---|---|---|
| STEINLIN | A*0101 | B8 | C*0701 |
| LBUF | A*3001 | B*1302 | C*0601 |
| BM14 | A3 | B7 | C7 |
| JBUSH | A32 | B38 | C*1203 |
| BTB | A2 | B27 | C1 |
| WT47 | A32 | B44 | C5 |
| SWEIGOO7 | A*2902 | B*4002 | C*02022 |
| BM92 | A*2501 | B*5101 | C1 |
| SPL | A31 | B62 | C1 |
| SPOO10 | A2 | B*4402 | C5 |

Four URSTO probes (P3, P4, P5 and P29) labelled with DIG were then hybridised to these membranes under specific conditions: 54° C. for 90 minutes in TMACl solution. The membranes were then washed (X3) under stringent conditions: 58° C. for 10 min in TMACl wash solution. Detection was performed by anti-DIG alkaline-phosphatase conjugate, followed by development with CSPD.

It was found that the four URSTO probes gave the expected pattern (see the following table).

| | Results of 4 URSTO probes | | | |
|---|---|---|---|---|
| Allelic | URSTO probes | | | |
| specificity | P3 | P4 | P5 | P29 |
| A*0101 | − | − | − | − |
| B8 | − | − | − | − |
| C*0701 | − | − | − | − |
| A*3001 | − | − | − | + |
| B*1302 | − | − | − | − |
| C*0601 | − | − | − | − |
| A3 | − | − | − | + |
| B7 | − | − | − | − |
| C7 | − | − | − | − |
| A32 | − | + | − | − |
| B38 | − | + | − | − |
| C*1203 | − | − | − | − |
| A2 | − | − | − | + |
| B27 | − | − | − | − |
| C1 | − | − | − | − |
| A32 | − | + | − | − |
| B44 | − | − | + | − |
| C5 | − | − | − | − |
| A*2902 | − | − | − | − |
| B*4002 | − | − | − | − |
| C*02022 | − | − | − | − |
| A*2501 | − | + | − | − |
| B5101 | − | + | + | − |
| C1 | − | − | − | − |
| A31 | + | − | − | + |
| B62 | − | − | + | − |
| C1 | − | − | − | − |
| A2 | − | − | − | + |
| B*4402 | − | − | + | − |
| C5 | − | − | − | − |

Tests with all 40 probes and a large number of internationally defined samples (International Histocompatibility workshop cell lines) indicate that each allele tested gave the pattern shown in Table 2 (see FIGS. 3 and 4).

A list of HLA class I alleles which have been isolated and identified by URSTO is set out in the following table:

| HLA class I alleles which have been isolated and identified by URSTO method |
|---|
| HLA-A (n = 33) |
| A*0101, A*0102, A*0201, A*0202, A*0203, A*0204, A*0205, A*0206, A*0207, A*0209, A*0209, A*0210, A*0211, A*0212, A*0213, A*0216, A*0217, A*0301, A*1101, A*2301, A*2402, A*2403, A*2501, A*2601, A*2902, A*3001, A*3002, A*3101, A*3201, A*3301, A*6601, A*6602, A*6802 |
| HLA-B (n = 30) |
| B*0702, B*0801, B*1302, B*1402, B*1501, B*1502, B*1520, B*1801, B*3501, B*3701, B*3801, B*4001, B*4002, B*4101, B*4201, B*4402, B*4403, B*4601, B*4701, B*4801, B*4901, B*5001, B*5101, B*5201, B*5301, B*5502, B*5701, B*5801, B*5802, B*6701 |
| HLA-Cw (n = 18) |
| Cw*0102, Cw*0202, Cw*0302, Cw*0303, Cw*0304, Cw*0401, Cw*0501, Cw*0602, Cw*0701, Cw*0702, Cw*0704, Cw*0802, Cw*1202, Cw*1203, Cw*1402, Cw*1502, Cw*1601, Cw*1701 |

Number of different heterozygous combinations tested: HLA-A 19, HLA-B 14, and HLA-Cw 11.

In the identification of the alleles set out in the above table, DNA was extracted from 63 B-lymphoblastoid cell lines; these included 22 heterozygous and 41 homozygous lines. After PCR amplification with locus specific primers as described above the anti-sense single strands were isolated and hybridised as described above with the appropriate reference strands (A*0101, B*4402, Cw*0701).

The allelic bands were resolved in non-denaturing PAGE and eluted from low melting point agarose as described above. The DNA from the isolated bands was blotted on nylon membranes (as in FIG. 3) and hybridised with URSTO probes. Alleles were identified by comparison of patterns with those in Table 2.

REAGENTS

A) Nucleotide Sequences of Primers Used for Locus-specific Amplification:

5' A locus primer (SEQ ID NO:41): GAA ACG/C GCC TCT GT/CG GGG AGA AGC AA (Intron 1; 21–46)

3' A locus primer (SEQ ID NO:42): TGT TGG TCC CAA TTG TCT CCC CTC (Intron 3: 66–89)

5' B locus primer (SEQ ID NO:43): GGG AGG AGC GAG GGG ACC G/CCA G (Intron 1: 36–57)

3' B locus primer (SEQ ID NO:44): GGA GGC CAT CCC CGG CGA CCT AT (Intron 3: 37–59)

5' C locus primer (SEQ ID NO:45): AGC GAG GG/TG CCC GCC CGG CGA (Intron 1: 42–61)

3' C locus primer (SEQ ID NO:46): GGA GAT GGG GAA GGC TCC CCA CT (Intron 3: 12–35)

B) Buffers:

| Washing buffer: | 10 mM | Tris-HCl pH 7.5 |
|---|---|---|
|  | 1.0 mM | EDTA |
|  | 2.0 M | NaCl |
| Hybridisation buffer: | 20 mM | Tris-HCl pH 8.4 |
|  | 50 mM | KCl |
| PCR buffer: | 20 mM | Tris-HCl pH 8.4 |
|  | 50 mM | KCl |

| -continued | | |
|---|---|---|
|  | 0.2 mM | MgCl2 |
| TE buffer | 10 mM | Tris-HCl pH 7.5 |
|  | 1 mM | EDTA |

C) Various

Dynabeads M-280 Streptavidin (10 mg/ml)

Magnetic particle concentrator-Dynal MPC

Nylon membranes, positively charged (Boehringer Mannheim)

CSPD-Disodium3-(4-methoxyspiro{1,2-dioxetane-3,2'-(5' cholo)t ricyclo[3.3.1.13,7] decan}-4-yl) Boehringer Mannheim DIG Oligonucleotide 3'-End Labeling Kit (Boehringer Mannheim)

Anti-digoxigenin-AP Fab fragments (Boehringer Mannheim)

A Thermal cycler (PTC-200 Peltier Thermal Cycler MJ Research)

Ultrapure dNTP set, 2'-Deoxynucleoside 5'-Triphosphate (Pharmacia Biotech)

Taq DNA Polymerase (Gibco BRL)

50 mM MgCl2

0.1 M NaOH

SeaPlaque Agarose (Flowgen Instruments Ltd)

Protogel, 30% Acrylamide and 0.8% Bisacrylamide (National Diagnostics)

REFERENCES

1. —D. Weisdorf, R. Haake & B. Blazar. Risk factors for acute graft-versus-host disease in histocompatible donor bone marrow transplantation. *Transplantation* 1991: 51: 1197–1203

2. —L. A. Ochs, W. J. Miller, A. H. Filipovich, R. J. Haake, P. B. McGlave, B. R. Blazar, N. K. C. Ramsay, J. H. Kersey & D. J. Weisdorf. Predictive factors for chronic graft-versus-host disease after histocompatible sibling donor bone marrow transplantation. *Bone Marrow Transplant* 1994: 13; 455–460

3. —L. A Smyth, C. S. Witt, F. T. Christiansen, R. P. Hermann, P. N. Hollingsworth, D. C. Townend, E Edward & R. L. Dawking. The MHC influences acute graft versus host disease in MHC matched adults undergoing allogeneic one marrow transplantation. *Bone Marrow Transplant* 1993: 12; 351–355

4. —A. Bacigalupo, F. Gualandi, M. T. Van Lint, M. Sessarego, F. Frassoni, D. Occhini, T. Lamparelli, R. Oneto, V. Vitale, R. Corvo, E. Raul de la Torre & A. M. Marmont. Multivariate analysis of risk factors for survival and relapse in chronic granulocytic leukemia following allogeneic marrow transplantation: impact of disease related variables (Sokal score). *Bone Marrow Transplant* 1993: 12; 443–448

5. —J. Sierra, A. Graneda, J. Garcia, A. Valls, E. Carreras, M. Rovira, C. Canals, E. Martinez, C. Punti, M. Algara, P. Martin, A. Merino, M. J. Terol, A. Urbano Ispizua & C. Rozman. Autologous bone marrow transplantation for acute leukemia: results and prognostic factors in 90 consecutive patients. *Bone Marrow Transplant* 1993: 12; 517–523

6. —J. L. Bidwell. Applications of the polymerase chain reaction to HLA class II typing. *Vox Sang* 1992: 63: 81–89

7. —P. Parham, E. Adams & k. L. Arnett. The Origins of HLA-A, B, C Polymorphism. *Immunological Reviews* 1995: 143; 141–180

8. —P. Krausa, M. Brywka III, D. Savage, K. M. Hui, M. Bunce, J. L. F. Ngai, D. L. T. Teo, Y. W. Ong, D. Barouch, C. E. M. Allsop, A. V. S. Hill, A. J. McMichael, J. G. Bodmer & M. J. Browning. Genetic polymorphism within HLA-A*02: significant allelic variation revealed in different populations. *Tissue Antigens* 1995: 45; 223–231

9. —P. Krausa, J. G. Bodmer, M. J. Browning. Defining the common subtypes of HLA A9, A10, A28 and A19 by use of ARMS/PCR. *Tissue Antigens* 1993: 42; 91–99

10. —C. W. Summers, V. J. Hampson & G. M. Taylor. HLA class I non-coding nucleotide sequences, 1992. *European Journal of Immunogenetics* 1993: 20; 201–240

11. —S. Hoshino, A. Kimura, Y. Fukuda, K. Dohi & T. Sasazuki. Polymerase chain reaction-single-strand conformation polymorphism analysis of polymorphism in DPA1 and DPB1 genes: A simple, economical, and rapid method for histocompatibility testing. *Human Immunology* 1992: 33; 98–107

12. —M. Orita, Y. Suzuki, T. Sekiya & K. Hayashi. Rapid and sensitive detection of point mutations and DNA polymorphisms using the polymerase chain reaction. *Genomics* 1989: 5; 874–879

13. —Y. Suzuki, T. Sekiya & K. Hayashi. Allele-specific polymerase chain reaction: A method for amplification and sequence determination of a single component among a mixture of sequence variants. *Analytical Biochemistry* 1991: 192; 82–84

14. —R. Blasczyk, U. Hahn, J. Wehling, D. Huhn & A. Salama. Complete subtyping of the HLA-A locus by sequence-specific amplification followed by direct sequencing or single-strand conformation polymorphism analysis. *Tissue Antigens* 1995: 46; 86–95

15. —R. Blasczyk, J. Wehling, B. S. Kubens, U. Hahn, D. Huhn & A. Salama. A novel HLA-A24 allele (A*2405) identified by single-strand conformation polymorphism analysis and confirmed by solid-phase sequencing and isoelectric focusing. *Tissue Antigens* 1995: 46; 54–58

16. —M. Orita, H. Iwahana, H. Kanazawa, K. Hayashi and T. Sekiya. Detection of polymorphism of human DNA by gel electrophoresis as single-strand conformation polymorphism. *Proc Natl Acad Sci USA* 1989: 86; 2766–2770

17. —G. Fischer and L. S Lerman. DNA fragments differing by a single base-pair substitution are separated in denaturing gradient gels: Correspondence with melting theory. *Proc Natl Acad Sci USA* 1983: 80; 1579–1583

18. —K. Henco and M. Heibey. Quantitative PCR: the determination of template number copy numbers by temperature gradient gel electrophoresis. *Nucleic Acid Res* 1990: 18; 6733–6734

19. —T. M. Clay, J. L. Bidwell, M. R. Howard & B. A. Bradley. PCR-fingerprinting for selection of HLA matched unrelated marrow donors. *Lances* 1991; 337; 1049–52

20. —A. Bhattacharyya & D. M. J. Lilley. The contrasting structures of mismatched DNA sequences containing looped-out bases (bulges) and multiple mismatches (bubbles). *Nucleic Acids Res* 1989: 17; 6821–6840

21. —F. Aboul-ela, D. Koh & I. Tinoco. Base-base mismatches. Thermodynamics of double helix formation for dCA3XA3G+dCT3YT3G (X, Y=A, C, G, T) *Nucleic Acids Res* 1985: 13; 4811–4824

22. —J. Y. Tong, A. Hammad, W. A. Rudert, M. Trucco & S. Hsia. Heteroduplexes for HLA DQB1 identity of family members and kidney donor-recipient pairs. *Transplantation* 1994: 57; 741–745

23. —R. Sorrentino, I. Cascino & R. Tosi. Subgrouping of DR4 alleles by DNA heteroduplex analysis. *Human Immunology* 1992: 33; 18–23

24. —M. White, M. Carvalho, D. Derse, S. O'Brien & M. Dean. Detecting single base substitutions as heteroduplex polymorphisms. *Genomics* 1992: 12; 301–306

25. —M. Carrington, M. White, M. Dean, D. Mann & F. E. Ward. The use of DNA heteroduplex patterns to map recombination within the HLA class II region. *Human Immunology* 1992: 33; 114–121

26. —N. A. P. Wood, T. M. Clay & J. L. Bidwell. HLA-DR/Dw matching by PCR Fingerprinting: The origin of PCR fingerprints and further applications. *European Journal of Immunogenetics* 1991; 18; 147–153

27. —M. Allen, L. Liu & U. Gyllensten. A comprehensive polymerase chain reaction-oligonucleotide typing system for HLA class I A locus. *Human Immunology* 1994. 40; 25–32

28. —X. Gao, I. B. Jakobsen & S. W. Serjeantson. Characterization of the HLA-A polymorphism by locus-specific polymerase chain reaction amplification and oligonucleotide hybridization. *Human Immunology* 1994: 41; 267–279

29. —A. Selvakumar, C. B. Granja, M. Salazar, S. M. Alosco, E. J. Yunis & B. Dupont. A novel subtype of A2 (A*0217) isolated from the South American Indian B-cell line AMALA. *Tissue Antigens* 1995: 45; 343–347

30. —E. W. Petersdorf & J. A. Hansen. A comprehensive approach for typing the alleles of the HLA-B locus by automated sequencing. *Tissue Antigens* 1995: 46; 73–85

31. —J. A. Madrigal, M. P. Belich, W. H. Hildebrand, R. J. Benjamin, A. M. Little, J. Zemmour, P. D. Ennis, F. E. Ward, M. L. Petzl-Erler, E. D. du Toit & P. Parham.Distinctive HLA-A, B antigens of black populations formed by interallelic conversion. *J. Immunol* 1992: 149; 3411–3415

32. —J. Zemmour & P. Parham. HLA Class I Nucleotide Sequences, 1992. *European Journal of Immunogenetics* 1993: 20; 29–45.

33. —N. Cereb, P. Maye, S. Lee, Y. Kong & S. Y. Yang. Locus-specific amplification of HLA class I genes from genomic DNA. *Tissue Antigens* 1995:

34. —J. A. Madrigal, W. H. Hildebrand, M. P. Belich, R. J. Benjamin, A. M. Little, J. Zemmour, P. D. Ennis, F. E. Ward, M. L. Petzl-Erler, E. D. du Toit & P. Parham. Structural diversity in the HLA-A10 family of alleles: Correlations with serology. *Tissue Antigens* 1993: 41; 72–80

35. —D. Chen, W. Endres, S. A. Meyer & W. Stangel. A polymerase chain reaction-sequence-specific oligonucleotide procedure for HLA class II typig using biotin- and digoxigenin-labelled probes simultaneously in hybridization. *Human Immunology* 1994: 39; 25–30

36. —GE Hawes, L Struyk, PJ van den Elsen. Differential usage of T cell receptor V gene segments in CD4+and CD8+subsets of T lymphocytes in monozygotic twins, *J. Immunol* 1993:150; 2033–2045

37. —C Giachino, MP Rocci, G De Libero, G Oderda, N Ansaldi and N Migone. An alternative approach to the assessment of T cell clonality in celiac disease intestinal lesions through cDNA heteroduplex analysis of T-cell receptor VJ junctions. *Human Immunology* 1994: 40; 303–311

38. —R. Arguello, H. Avakian, J. H. Goldman and J. A. Madrigal. A novel method for simultaneous high resolution identification of HLA-A, HLA-B and HLA-Cw alleles. *Proc Natl Acad Sci. USA* 1996: 93; 10961–10965

What is claimed is:

1. A method for identifying an unknown allele of a polyallelic gene, which method comprises:

(i) separating the allele from a mixture of alleles of the polyallelic gene by:
  (a) amplifying the alleles in the mixture of alleles;
  (b) hybridizing single strands of the amplified alleles with a complementary strand of a reference allele to form duplexes;
  (c) separating the alleles;

(ii) contacting the unknown allele with a panel of probes, each of which recognises a sequence motif that is present in some alleles of the polyallelic gene but not in others;

(iii) observing which probes recognise the unknown allele so as to obtain a fingerprint of the unknown allele; and (iv) comparing the fingerprint with the fingerprint of known alleles.

2. A method according to claim 1 wherein the polyallelic gene is a human leucocyte antigen (HLA) gene.

3. A method according to claim 2 wherein the HLA gene is an HLA class I gene or an HLA class II gene.

4. A method according to claim 1 wherein the panel of probes consists of from 20 to 70 probes.

5. A method according to claim 3 wherein the HLA gene is an HLA class I gene and the panel of probes comprises from 20 to 40 probes selected from the group of probe sequences consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and sequences complementary thereto.

6. A method according to claim 3 wherein each of the probes has a sequence at least 40% identical to a sequence selected from the group of probe sequences consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and sequences complementary thereto.

7. A method according to claim 5 wherein the panel of probes comprises the 40 probes consisting of the group of probe sequences SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 34, 36, 37, 38, 39, and 40, and sequences complementary thereto.

8. A method according to claim 1 wherein the allele is separated from the mixture of alleles, the separation comprising (i) amplifying the mixture of alleles employing a pair of primers in which one of the primers carries a ligand, so as to produce an amplified mixture of double-stranded alleles in which one of the strands carries a ligand;

(ii) contacting the amplified mixture of double-stranded alleles with a receptor on a solid support under conditions such that the ligand binds to the receptor;

(iii) separating the mixture of double-stranded alleles into single-strands and removing the strands that are not bound to the support by the ligand;

(iv) recovering the remaining strands from the support;

(v) mixing the recovered strands with a complementary strand of a reference allele so as to form duplexes; and (vi) separating the duplexes.

9. A method according to claim 8, modified by recovering the strands that do not bind to the support instead of those that bind to the support, and mixing these recovered strands with the reference allele strand in step (v).

10. A kit for identifying an unknown allele of a polyallelic gene, which kit comprises a panel of probes, each of which probes recognizes a sequence motif that is present in some alleles of the polyallelic gene but not in others, wherein the panel of probes is selected so as to recognise motifs of an HLA class I gene and the panel of probes comprises from 20 to 40 probes selected from the group of probe sequences consisting of SEQ ID NO: 1, 2, 3, 4, 5, 6, 7, 8, 9, 10, 11, 12, 13, 14, 15, 16, 17, 18, 19, 20,21, 22, 23, 24, 25, 26, 27, 28, 29, 30, 31, 32, 33, 34, 35, 36, 37, 38, 39, and 40, and sequences complementary thereto.

11. A kit for identifying an unknown allele of a polyallelic gene, which kit comprises a panel of at least three probes, each of which probes recognises a sequence motif that is present in some alleles of the polyallelic gene but not in others, wherein the panel of probes is selected so as to recognise motifs of an HLA class I gene and wherein each one of the probes has a sequence at least 40% identical to a sequence of one of the probes selected from the group of probe sequences consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and sequences complementary thereto.

12. A kit according to claim 10 wherein the panel of probes comprises 40 probes consisting of the group of probe sequences SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 35, 36, 37, 38, 39, and 40.

13. A composition comprising at least three probes selected from the group of probe sequences consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and sequences complementary thereto.

14. A composition according to claim 13, comprising at least twenty probes.

* * * * *